US012753216B2

(12) United States Patent
Dempsey et al.

(10) Patent No.: US 12,753,216 B2
(45) Date of Patent: Oct. 6, 2026

(54) BIOACTIVE AGENTS AND METHODS RELATED THERETO

(71) Applicant: AROA BIOSURGERY LIMITED, Auckland (NZ)

(72) Inventors: Sandi Grainne Dempsey, Auckland (NZ); Barnaby Charles Hough May, Auckland (NZ); Darren John Day, Wellington (NZ)

(73) Assignee: AROA BIOSURGERY LIMITED, Auckland (NZ)

( * ) Notice: Subject to any disclaimer, the term of this patent is extended or adjusted under 35 U.S.C. 154(b) by 1075 days.

(21) Appl. No.: 17/616,496

(22) PCT Filed: Jun. 5, 2020

(86) PCT No.: PCT/NZ2020/050058
§ 371 (c)(1),
(2) Date: Dec. 3, 2021

(87) PCT Pub. No.: WO2020/246900
PCT Pub. Date: Dec. 10, 2020

(65) Prior Publication Data

US 2022/0289804 A1 Sep. 15, 2022

Related U.S. Application Data

(60) Provisional application No. 63/014,530, filed on Apr. 23, 2020, provisional application No. 62/857,900, filed on Jun. 6, 2019.

(51) Int. Cl.

| | |
|---|---|
| ***C07K 14/00*** | (2006.01) |
| ***A61P 43/00*** | (2006.01) |
| ***C07K 14/47*** | (2006.01) |
| ***C12N 5/00*** | (2006.01) |
| ***G01N 33/50*** | (2006.01) |
| ***G01N 33/68*** | (2006.01) |

(52) U.S. Cl.
CPC .......... *C07K 14/4725* (2013.01); *A61P 43/00* (2018.01); *C12N 5/0068* (2013.01); *G01N 33/5008* (2013.01); *G01N 33/6887* (2013.01)

(58) Field of Classification Search
CPC .............. C07K 2317/24; C07K 14/525; C07K 16/283; A61K 40/42; A61K 38/00; A61K 40/10; A61K 38/39; A61P 11/00; A61P 11/06; A61P 19/04; A61P 29/00
See application file for complete search history.

(56) References Cited

U.S. PATENT DOCUMENTS

| | | | |
|---|---|---|---|
| 5,705,609 | A | 1/1998 | Ruoslahti et al. |
| 2002/0148351 | A1 | 10/2002 | Anderson et al. |
| 2003/0124152 | A1 | 7/2003 | Pang |
| 2003/0148351 | A1 | 8/2003 | Henry et al. |

FOREIGN PATENT DOCUMENTS

| | | | |
|---|---|---|---|
| WO | 9000194 | A1 | 1/1990 |
| WO | 1993/009800 | A1 | 5/1993 |
| WO | 9320202 | A1 | 10/1993 |
| WO | 2007/035363 | A2 | 3/2007 |
| WO | 2007035843 | A3 | 7/2007 |
| WO | 2014/018813 | A1 | 1/2014 |
| WO | 2020/246900 | A1 | 12/2020 |

OTHER PUBLICATIONS

Kisselev L., (Structure, 2002, vol. 10: 8-9).*
Kwiatkowski et al., (Biochemistry 38:11643-11650, 1999.*
Wristlock et al., (Quarterly Reviews of Biophysics 2003, vol. 36 (3): 307-340.*
Davos et al., (Proteins: Structure, Function and Genetics, 2000, vol. 41: 98-107.*
Aguado, B.A. et al. "Extracellular matrix mediators of metastatic cell colonization characterized using scaffold mimics of the pre-metastatic niche." Acta Biomaterialia, vol. 33:13-24 (2016).
Booth, A.J. et al. "Acellular Lnormal and fibrotic human lung matrices as a culture system for in vitro investigation." American Journal of Respiratory and Critical Care Medicine, vol. 186 (9): 866-876. (2012).
International Preliminary Report on Patentability, PCT/NZ2020/050058, dated Dec. 7, 2021, 11 pages.
International Search Report and Written Opinion, PCT/NZ2020/050058, dated Oct. 9, 2020, 10 pages.
Reing, J.E. et al. "Degradation Products of PExtracellular I-Matrix I-IAffect I—Cell P1 Migration—and Proliferation." Tissue Engineering, Part A, vol. 15(3): 605-614 (2009).
Robert, A.W. et al. "Tissue-Derived Signals for Mesenchymal Stem-Cell P Stimulation: Role of Cardiac and Umbilical Cord Microenvironments," Cells Tissues Organs, vol. 203 (3): 173-182 (2017).
Uniprot Accession No. Q9TTE2 May 1, 2000.
Werb, Z. et al. "Degradation of connective tissue matrices by macrophages. III. Morphological and biochemical studies on extracellular, pericellular, and intracellular events in matrix proteolysis by macrophages in culture," Journal of Experimental Medicine, vol. 152,(6): 1537-1553 (1980).
Wu, W. et al., "Characterization of decorin mRNA in pregnant intrauterine tissues of the ewe and regulation by steroids." American Journal of Physiology Cell Physiology, vol. 278(1, ptl): C199-C206 (2000).

(Continued)

*Primary Examiner* — Tekchand Saidha
*Assistant Examiner* — Mohammad Y Meah
(74) *Attorney, Agent, or Firm* — Nelson Mullins Riley & Scarborough LLP; Jane E. Remillard, Esq.; Jeanne M. DiGiorgio

(57) ABSTRACT

The present invention relates to methods for the detection, identification and use of one or more bioactive agents obtained from extracellular matrix in the presence of one or more cells, such as one or more cell-signalling polypeptides, and said bioactive agents. Research, diagnostic and therapeutic methods utilising such bioactive agents are also provided.

11 Claims, 11 Drawing Sheets

Specification includes a Sequence Listing.

(56) References Cited

OTHER PUBLICATIONS

Dempsey S.et al., A novel chemotactic factor derived from the extracellular matrix protein decorin recruits mesenchymal stromal cells in vitro and in vivo PLoS ONE 15(7): e0235784, 24 pages (2020) https://doi.org/10.1371/journal. pone.0235784.
Extended European Search Report, EP Applicatio No. 20817784, dated Jul. 7, 2023, 14 pages.
Seidler D. "The galactosaminoglycan-containing decorin and its impact on diseases," Current Opinion in Structural Biology, vol. 22(5):578-582 (2012).
International Search Report and Written Opinion, PCT/NZ2024/050004, dated Apr. 23, 2024, 14 pages.
International Search Report and Written Opinion, PCT/NZ2024/050006, dated Apr. 2, 2024, 14 pages.
International Search Report and Written Opinion, PCT/NZ2024/050005, dated Apr. 23, 2024, 14 pages.
Heinegård, D. et al., "The core proteins of large and small interstitial proteoglycans from various connective tissues form distinct subgroups," Biochemical Journal, 230(1): 181-194 (1985).
Neill, T. et al., "Decorin as a multivalent therapeutic agent against cancer," Advanced Drug Delivery Reviews, vol. 97: 174-185 (2016).
McEwan, P. et al., "Structural correlations in the family of small leucine-rich repeat proteins and proteoglycans," J Struct Biol., vol. 155(2):294-305 (2006).

* cited by examiner

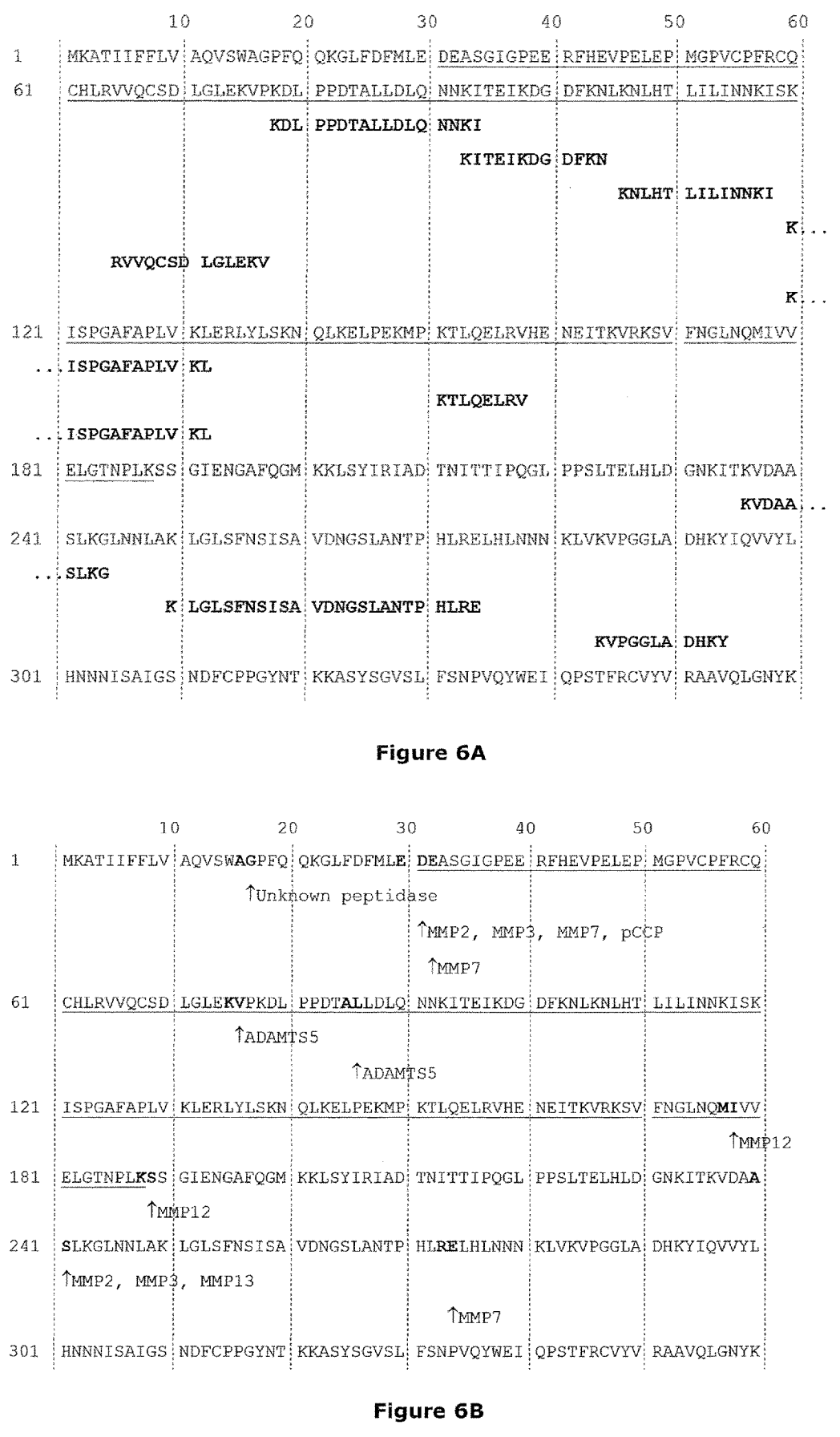

```
             10         20         30         40         50         60
1     MKATIIFFLV AQVSWAGPFQ QKGLFDFMLE DEASGIGPEE RFHEVPELEP MGPVCPFRCQ
61    CHLRVVQCSD LGLEKVPKDL PPDTALLDLQ NNKITEIKDG DFKNLKNLHT LILINNKISK
                         KDL PPDTALLDLQ NNKI
                                      KITEIKDG DFKN
                                                  KNLHT LILINNKI
                                                                 K...
         RVVQCSD LGLEKV
                                                                 K...
121   ISPGAFAPLV KLERLYLSKN QLKELPEKMP KTLQELRVHE NEITKVRKSV FNGLNQMIVV
   ...ISPGAFAPLV KL
                                      KTLQELRV
   ...ISPGAFAPLV KL
181   ELGTNPLKSS GIENGAFQGM KKLSYIRIAD TNITTIPQGL PPSLTELHLD GNKITKVDAA
                                                                 KVDAA...
241   SLKGLNNLAK LGLSFNSISA VDNGSLANTP HLRELHLNNN KLVKVPGGLA DHKYIQVVYL
   ...SLKG
               K LGLSFNSISA VDNGSLANTP HLRE
                                                KVPGGLA DHKY
301   HNNNISAIGS NDFCPPGYNT KKASYSGVSL FSNPVQYWEI QPSTFRCVYV RAAVQLGNYK
```

Figure 6A

```
             10         20         30         40         50         60
1     MKATIIFFLV AQVSWAGPFQ QKGLFDFMLE DEASGIGPEE RFHEVPELEP MGPVCPFRCQ
                      ↑Unknown peptidase
                                  ↑MMP2, MMP3, MMP7, pCCP
                                   ↑MMP7
61    CHLRVVQCSD LGLEKVPKDL PPDTALLDLQ NNKITEIKDG DFKNLKNLHT LILINNKISK
                     ↑ADAMTS5
                               ↑ADAMTS5
121   ISPGAFAPLV KLERLYLSKN QLKELPEKMP KTLQELRVHE NEITKVRKSV FNGLNQMIVV
                                                                ↑MMP12
181   ELGTNPLKSS GIENGAFQGM KKLSYIRIAD TNITTIPQGL PPSLTELHLD GNKITKVDAA
             ↑MMP12
241   SLKGLNNLAK LGLSFNSISA VDNGSLANTP HLRELHLNNN KLVKVPGGLA DHKYIQVVYL
      ↑MMP2, MMP3, MMP13
                                    ↑MMP7
301   HNNNISAIGS NDFCPPGYNT KKASYSGVSL FSNPVQYWEI QPSTFRCVYV RAAVQLGNYK
```

Figure 6B

BIOACTIVE AGENTS AND METHODS RELATED THERETO

CROSS-REFERENCE TO RELATED APPLICATIONS

This application is a 35 U.S.C. 371 national stage filing of International Application No. PCT/NZ2020/050058, filed Jun. 5, 2020, which claims priority to U.S. Provisional Application 62/857,900, filed Jun. 6, 2019 and to U.S. Provisional Application 63/014,530, filed on Apr. 23, 2020. The contents of the aforementioned applications are hereby incorporated by reference in their entirety.

SEQUENCE LISTING

The instant application contains a Sequence Listing which has been submitted in ASCII format via EFS-Web, and is hereby incorporated by reference in its entirety. Said ASCII copy, created on Dec. 3, 2021, is named SL_MSJ 011US.txt and is 7,570 bytes in size.

TECHNICAL FIELD

The invention relates to bioactive agents, including therapeutic agents, and methods of identifying same in selected biological samples. More particularly, the method relates to the use of cells interacting in vitro with extracellular matrix such as acellular extracellular matrix or decellularized extracellular matrix, whereby the interaction liberates one or more bioactive agents of interest, including one or more bioactive agents having potential therapeutic efficacy. In a further aspect, the invention relates to the identification, characterisation, and use of one such bioactive agent, a polypeptide fragment of the extracellular matrix protein Decorin having stem cell recruiting activity.

BACKGROUND OF THE INVENTION

The following includes information that may be useful in understanding the present inventions. It is not an admission that any of the information provided herein is prior art, or relevant, to the presently described or claimed inventions, or that any publication or document that is specifically or implicitly referenced is prior art. Any discussion of the prior art throughout the specification should in no way be considered as an admission that such prior art is widely known or forms part of the common general knowledge in the field.

It will be appreciated that there is an ongoing need for bioactive agents, including bioactive agents having therapeutic activity, for a range of research and therapeutic uses. While extensive research and development efforts have focused on synthetic agents, bioactive agents derived from biological systems are of significant interest.

Generally, bioactive agents originating from tissue, including for example extracellular matrix (ECM), have been identified from intact tissues via serendipity or targeted methods. However, in the case of bioactive agents from ECM, these methods face a number of challenges. For example, tissues are complex and highly heterogeneous materials, comprising not only various cell types but the ECM itself. As such, the identification of agents from the complex mixture that is normal tissue requires various fractionation, separation, and analytical techniques that may miss potentially useful bioactive agents, including therapeutic agents. Furthermore, it is believed that the biological properties of ECM and components thereof are dependent on a number of factors, including the age of the tissue, the tissue location, and any disease state. Also, the ECM and inter-related cell population are involved in a wide variety of signaling processes, mediated via various bioactive agents. These signaling events may be continuous or transient and are dependent on the ECM components and cell(s) involved. This gives rise to the potential for important bioactive agents being only transient or short lived in tissues, thus making their identification challenging. Existing methods are therefore limited by the complexity of tissue ECM, the relative abundance of potential therapeutic agents in the ECM, the complex interactions taking place in tissue ECM, and the practical challenges of separating and identifying bioactive agents.

As such, new methods for identifying potentially therapeutic biomolecules from ECM, including acellular extracellular matrix (aECM) or decellularized extracellular matrix (dECM) materials, are required to overcome these limitations.

However, currently there are no effective and convenient methods suitable for identification of bioactive agents derived from the interaction of cells with ECM, particularly those suitable for identification of bioactive agents from the interaction of one or more cell populations with ECM, including aECM and dECM.

There is thus a need to develop new and improved methods for the identification of such agents, and a related need for such agents themselves.

It is therefore an object of the invention to provide one or more bioactive agents, such as a bioactive polypeptide, and/or one or more methods of detectin/or identifying such agents, or to at least provide a useful alternative to existing methods, or to at least provide the public with a useful choice.

SUMMARY OF THE INVENTION

In a first aspect the invention relates to an isolated, purified, recombinant or synthetic polypeptide selected from the group comprising:

a) a polypeptide comprising, consisting essentially of, or consisting of an amino acid sequence corresponding to residues 1 to 188 of mammalian Decorin;

b) a polypeptide comprising, consisting essentially of, or consisting of an amino acid sequence corresponding to residues 31 to 188 of mammalian Decorin;

c) an N-terminal fragment of mammalian Decorin comprising, consisting essentially of, or consisting of at least 10 contiguous amino acids corresponding to any amino acid sequence within residues 1 to 188 of mammalian Decorin;

d) an N-terminal fragment of mammalian Decorin comprising, consisting essentially of, or consisting of at least 10 contiguous amino acids corresponding to any amino acid sequence within residues 31 to 188 of mammalian Decorin;

e) a polypeptide comprising, consisting essentially of, or consisting of an amino acid sequence corresponding to residues 1 to 177 of mammalian Decorin;

f) a polypeptide comprising, consisting essentially of, or consisting of an amino acid sequence corresponding to residues 31 to 177 of mammalian Decorin;

g) an N-terminal fragment of mammalian Decorin comprising, consisting essentially of, or consisting of at least 10 contiguous amino acids corresponding to any amino acid sequence within residues 1 to 177 of mammalian Decorin;

h) an N-terminal fragment of mammalian Decorin comprising, consisting essentially of, or consisting of at least 10 contiguous amino acids corresponding to any amino acid sequence within residues 31 to 177 of mammalian Decorin;

i) a polypeptide comprising, consisting essentially of, or consisting of an amino acid sequence corresponding to residues 1 to 170 of mammalian Decorin;

j) a polypeptide comprising, consisting essentially of, or consisting of an amino acid sequence corresponding to residues 31 to 170 of mammalian Decorin;

k) an N-terminal fragment of mammalian Decorin comprising, consisting essentially of, or consisting of at least 10 contiguous amino acids corresponding to any amino acid sequence within residues 1 to 170 of mammalian Decorin;

l) an N-terminal fragment of mammalian Decorin comprising, consisting essentially of, or consisting of at least 10 contiguous amino acids corresponding to any amino acid sequence within residues 31 to 170 of mammalian Decorin;

m) a polypeptide comprising, consisting essentially of, or consisting of the amino acid sequence depicted in any one of Sequence ID Nos: 1 to 4;

n) a polypeptide comprising, consisting essentially of, or consisting of at least about 10 contiguous amino acids from any one of a) to m) above;

o) a polypeptide comprising or consisting of at least about 10 contiguous amino acids from any one of a) to n) above, wherein said polypeptide comprises a motif or region capable of interacting with or recruiting one or more cells, including one or more stem cells;

p) a polypeptide comprising or consisting of at least about 10 contiguous amino acids from any one of a) to o) above, wherein said polypeptide comprises a motif or region capable of interacting with or recruiting one or more mesenchymal stem cells;

q) a functional fragment, a functional variant, a peptide analogue or peptidomimetic, or a derivative of any one of a) to p) above; and r) a polypeptide having at least about 70% amino acid identity to any one of a) to q) above.

Any of the embodiments described herein can relate to any of the aspects presented herein.

Another aspect of the present invention relates to a composition, including a pharmaceutical composition, comprising one or more polypeptides selected from the group comprising:

a) a polypeptide comprising, consisting essentially of, or consisting of an amino acid sequence corresponding to residues 1 to 188 of mammalian Decorin;

b) a polypeptide comprising, consisting essentially of, or consisting of an amino acid sequence corresponding to residues 31 to 188 of mammalian Decorin;

c) an N-terminal fragment of mammalian Decorin comprising, consisting essentially of, or consisting of at least 10 contiguous amino acids corresponding to any amino acid sequence within residues 1 to 188 of mammalian Decorin;

d) an N-terminal fragment of mammalian Decorin comprising, consisting essentially of, or consisting of at least 10 contiguous amino acids corresponding to any amino acid sequence within residues 31 to 188 of mammalian Decorin;

e) a polypeptide comprising, consisting essentially of, or consisting of an amino acid sequence corresponding to residues 1 to 177 of mammalian Decorin;

f) a polypeptide comprising, consisting essentially of, or consisting of an amino acid sequence corresponding to residues 31 to 177 of mammalian Decorin;

g) an N-terminal fragment of mammalian Decorin comprising, consisting essentially of, or consisting of at least 10 contiguous amino acids corresponding to any amino acid sequence within residues 1 to 177 of mammalian Decorin;

h) an N-terminal fragment of mammalian Decorin comprising, consisting essentially of, or consisting of at least 10 contiguous amino acids corresponding to any amino acid sequence within residues 31 to 177 of mammalian Decorin;

i) a polypeptide comprising, consisting essentially of, or consisting of an amino acid sequence corresponding to residues 1 to 170 of mammalian Decorin;

j) a polypeptide comprising, consisting essentially of, or consisting of an amino acid sequence corresponding to residues 31 to 170 of mammalian Decorin;

k) an N-terminal fragment of mammalian Decorin comprising, consisting essentially of, or consisting of at least 10 contiguous amino acids corresponding to any amino acid sequence within residues 1 to 170 of mammalian Decorin;

l) an N-terminal fragment of mammalian Decorin comprising, consisting essentially of, or consisting of at least 10 contiguous amino acids corresponding to any amino acid sequence within residues 31 to 170 of mammalian Decorin;

m) a polypeptide comprising, consisting essentially of, or consisting of the amino acid sequence depicted in any one of Sequence ID Nos: 1 to 4;

n) a polypeptide comprising, consisting essentially of, or consisting of at least about 10 contiguous amino acids from any one of a) to m) above;

o) a polypeptide comprising or consisting of at least about 10 contiguous amino acids from any one of a) to n) above, wherein said polypeptide comprises a motif or region capable of interacting with or recruiting one or more cells, including one or more stem cells; and p) a polypeptide comprising or consisting of at least about 10 contiguous amino acids from any one of a) to o) above, wherein said polypeptide comprises a motif or region capable of interacting with or recruiting one or more mesenchymal stem cells;

q) a functional fragment, a functional variant, a peptide analogue or peptidomimetic, or a derivative of any one of a) to p) above; and r) a polypeptide having at least about 70% amino acid identity to any one of a) to q) above.

s) any combination of any two or more of a) to r) above.

In one embodiment, the composition comprises a pharmaceutically acceptable carrier.

Another aspect of the present invention relates to a reagent comprising one or more polypeptides described herein, and/or a composition as described herein.

Another aspect of the present invention relates to a kit comprising a reagent and/or a composition as described herein.

According to another aspect, the invention relates to an expression construct comprising a nucleic acid encoding a polypeptide selected from the group comprising:

a) a polypeptide comprising, consisting essentially of, or consisting of an amino acid sequence corresponding to residues 1 to 188 of mammalian Decorin;

b) a polypeptide comprising, consisting essentially of, or consisting of an amino acid sequence corresponding to residues 31 to 188 of mammalian Decorin;
c) an N-terminal fragment of mammalian Decorin comprising, consisting essentially of, or consisting of at least 10 contiguous amino acids corresponding to any amino acid sequence within residues 1 to 188 of mammalian Decorin;
d) an N-terminal fragment of mammalian Decorin comprising, consisting essentially of, or consisting of at least 10 contiguous amino acids corresponding to any amino acid sequence within residues 31 to 188 of mammalian Decorin;
e) a polypeptide comprising, consisting essentially of, or consisting of an amino acid sequence corresponding to residues 1 to 177 of mammalian Decorin;
f) a polypeptide comprising, consisting essentially of, or consisting of an amino acid sequence corresponding to residues 31 to 177 of mammalian Decorin;
g) an N-terminal fragment of mammalian Decorin comprising, consisting essentially of, or consisting of at least 10 contiguous amino acids corresponding to any amino acid sequence within residues 1 to 177 of mammalian Decorin;
h) an N-terminal fragment of mammalian Decorin comprising, consisting essentially of, or consisting of at least 10 contiguous amino acids corresponding to any amino acid sequence within residues 31 to 177 of mammalian Decorin;
i) a polypeptide comprising, consisting essentially of, or consisting of an amino acid sequence corresponding to residues 1 to 170 of mammalian Decorin;
j) a polypeptide comprising, consisting essentially of, or consisting of an amino acid sequence corresponding to residues 31 to 170 of mammalian Decorin;
k) an N-terminal fragment of mammalian Decorin comprising, consisting essentially of, or consisting of at least 10 contiguous amino acids corresponding to any amino acid sequence within residues 1 to 170 of mammalian Decorin;
l) an N-terminal fragment of mammalian Decorin comprising, consisting essentially of, or consisting of at least 10 contiguous amino acids corresponding to any amino acid sequence within residues 31 to 170 of mammalian Decorin;
m) a polypeptide comprising, consisting essentially of, or consisting of the amino acid sequence depicted in any one of Sequence ID Nos: 1 to 4;
n) a polypeptide comprising, consisting essentially of, or consisting of at least about 10 contiguous amino acids from any one of a) to m) above;
o) a polypeptide comprising or consisting of at least about 10 contiguous amino acids from any one of a) to n) above, wherein said polypeptide comprises a motif or region capable of interacting with or recruiting one or more cells, including one or more stem cells; and
p) a polypeptide comprising or consisting of at least about 10 contiguous amino acids from any one of a) to o) above, wherein said polypeptide comprises a motif or region capable of interacting with or recruiting one or more mesenchymal stem cells;
q) a functional fragment, a functional variant, a peptide analogue or peptidomimetic, or a derivative of any one of a) to p) above; and
r) a polypeptide having at least about 70% amino acid identity to any one of a) to q) above.
s) any combination of any two or more of a) to r) above.

Another aspect of the present invention relates to a vector comprising an expression construct as described above.

Another aspect of the present invention relates to a host cell comprising an expression construct or a vector as defined above.

In a further aspect, the present invention relates to the use of a purified, isolated, recombinant or synthetic protein to mediate a biological effect, wherein the protein is selected from the group comprising:

a) a polypeptide comprising, consisting essentially of, or consisting of an amino acid sequence corresponding to residues 1 to 188 of mammalian Decorin;
b) a polypeptide comprising, consisting essentially of, or consisting of an amino acid sequence corresponding to residues 31 to 188 of mammalian Decorin;
c) an N-terminal fragment of mammalian Decorin comprising, consisting essentially of, or consisting of at least 10 contiguous amino acids corresponding to any amino acid sequence within residues 1 to 188 of mammalian Decorin;
d) an N-terminal fragment of mammalian Decorin comprising, consisting essentially of, or consisting of at least 10 contiguous amino acids corresponding to any amino acid sequence within residues 31 to 188 of mammalian Decorin;
e) a polypeptide comprising, consisting essentially of, or consisting of an amino acid sequence corresponding to residues 1 to 177 of mammalian Decorin;
f) a polypeptide comprising, consisting essentially of, or consisting of an amino acid sequence corresponding to residues 31 to 177 of mammalian Decorin;
g) an N-terminal fragment of mammalian Decorin comprising, consisting essentially of, or consisting of at least 10 contiguous amino acids corresponding to any amino acid sequence within residues 1 to 177 of mammalian Decorin;
h) an N-terminal fragment of mammalian Decorin comprising, consisting essentially of, or consisting of at least 10 contiguous amino acids corresponding to any amino acid sequence within residues 31 to 177 of mammalian Decorin;
i) a polypeptide comprising, consisting essentially of, or consisting of an amino acid sequence corresponding to residues 1 to 170 of mammalian Decorin;
j) a polypeptide comprising, consisting essentially of, or consisting of an amino acid sequence corresponding to residues 31 to 170 of mammalian Decorin;
k) an N-terminal fragment of mammalian Decorin comprising, consisting essentially of, or consisting of at least 10 contiguous amino acids corresponding to any amino acid sequence within residues 1 to 170 of mammalian Decorin;
l) an N-terminal fragment of mammalian Decorin comprising, consisting essentially of, or consisting of at least 10 contiguous amino acids corresponding to any amino acid sequence within residues 31 to 170 of mammalian Decorin;
m) a polypeptide comprising, consisting essentially of, or consisting of the amino acid sequence depicted in any one of Sequence ID Nos: 1 to 4;
n) a polypeptide comprising, consisting essentially of, or consisting of at least about 10 contiguous amino acids from any one of a) to m) above;
o) a polypeptide comprising or consisting of at least about 10 contiguous amino acids from any one of a) to n) above, wherein said polypeptide comprises a motif or region capable of interacting with or recruiting one or more cells, including one or more stem cells; and p) a polypeptide comprising or consisting of at least about 10 contiguous amino acids from any one of a) to o) above, wherein said polypeptide comprises a motif or region capable of interacting with or recruiting one or more mesenchymal stem cells;

q) a functional fragment, a functional variant, a peptide analogue or peptidomimetic, or a derivative of any one of a) to p) above; and r) a polypeptide having at least about 70% amino acid identity to any one of a) to q) above.

s) any combination of any two or more of a) to r) above.

In one embodiment, the biological effect is mediated in vivo in a subject in need thereof, for example by administration of the protein.

In another embodiment, the biological effect is mediated ex vivo, for example, in vitro, for example by contacting a biological sample with the protein. For example, the biological effect is mediated in vitro by contacting one or more cells, one or more tissues, or one or more organs with the protein.

In various embodiments the biological sample, tissue including aECM or dECM, or cells are from an animal, for example a mammalian subject, including a human subject, or a dairy animal, such as a cow, sheep, or goat.

In another aspect, the invention relates to a method of providing one or more bioactive agents, the method comprising the steps of:

i. providing extracellular matrix;

ii. contacting in vitro one or more cells with the extracellular matrix;

iii. optionally at least partially purifying one or more bioactive agents; and iv. recovering said one or more bioactive agents.

In another aspect, the invention relates to a method of detecting and/or identifying one or more bioactive agents, the method comprising the steps of:

i. providing extracellular matrix;

ii. contacting in vitro one or more cells with the extracellular matrix for a period sufficient to liberate one or more bioactive agents;

iii. optionally at least partially purifying one or more bioactive agents; and iv. detecting and/or identifying said one or more bioactive agents.

In various embodiments, the extracellular matrix is acellular ECM, decellularized ECM, or extracellular matrix is substantially free of cells, such as ECM substantially free of living cells. In one embodiment, the extracellular matrix is substantially free of endogenous cells, for example, is completely free of endogeneous cells.

In one embodiment, the acellular ECM is a naturally-occurring acellular ECM. For example, the acellular ECM is or is derived from vitreous humour.

In one embodiment, the extracellular matrix is decellularized extracellular matrix.

In various embodiments, the ECM is prepared from dermis, pericardium, stomach, small intestine, bladder, placenta, renal capsule, or lining of body cavities from any species of animal, including mammals, reptiles, avians, and insects.

In one embodiment, the ECM is ovine forestomach matrix (OFM).

In one embodiment, the period is sufficient to allow for interaction of one or more of the cells with the extracellular or a component thereof.

In one embodiment, the contacting is for a period sufficient to liberate one or more bioactive agents from the ECM. In one embodiment, the contacting is for a period sufficient to induce production or secretion of the bioactive agent by one or more of the cells.

In one embodiment, the period is from about 1 hour to about 7 days or more. In one example, the period is at least about 6 hours, at least about 12 hours, at least about 18 hours, or at least about 24 hours.

In one embodiment the one or more cells comprise an homogenous population of cells. In one example, the cells are macrophages, such as activated macrophages.

In one embodiment the one or more cells comprise two or more populations of cells. In one example, one population comprises macrophages, and/or one population comprises fibroblasts. In other examples, one or more cells comprise one or more neuronal cells, one or more epithelial cells, one or more endothelial cells, one or more stem cells, or one or more progenitor cells.

In various embodiments, the ECM and the one or more cells are each from a tissue or are each of a type that are not in contact with one another in vivo. For example, the acellular ECM and the one or more cells are each from a tissue or are each of a type that are not in contact with one another in a non-pathological state in vivo.

In various embodiments, when performed the at least partial purification comprises filtration, chromatography, such as HPLC and/or ion exchange, gel electrophoresis, sedimentation, or size exclusion including size exclusion filtration. In certain embodiments, more than one purification method is employed.

In various embodiments, purification and/or recovery is by chromatography, such as size exclusion chromatography, gel electrophoresis, or fast protein high pressure liquid chromatography.

In various embodiments, the detecting and/or identifying is by assaying one or more biological functions, such as the ability of the bioactive agent to elicit a biological response. For example, the detecting and/or identifying is by assaying chemotactic activity, modulation of one or more cellular responses, such as modulation of gene expression, modulation of cytokine or chemokine production, modulation of cell cycle progression, modulation of cellular differentiation or proliferation, modulation of cellular activation such as macrophage or neutrophil activation.

In various embodiments, the bioactivity of the bioactive agent is assessed in vitro or in vivo, and in certain embodiments includes but is not limited to such things as cell migration, chemotaxis, proliferation, or inhibition of cellular or enzymatic processes.

In various embodiments, the detecting and/or identifying is by direct detection and/or identification of the bioactive agent. For example, the detection and/or identification is by protein or nucleotide sequencing, by chromatography, by immunoassay, or by mass spectrometry.

In various embodiments, the one or more bioactive agents is a protein or peptide liberated by proteolytic cleavage, by cellular processing, for example by endocytosis and digestion of proteins using within an intracellular lysosome, by oxidative burst, or by conformational change.

Another aspect of the present invention relates to a composition comprising ECM and one or more cells, such as one or more exogeneous cells, including said composition for use in the identification of one or more bioactive agents.

In various embodiments, the extracellular matrix is acellular ECM, decellularized ECM, or extracellular matrix is substantially free of cells, such as ECM substantially free of living cells. In one embodiment, the extracellular matrix is substantially free of endogenous cells, for example, is completely free of endogeneous cells.

In one embodiment, the acellular ECM is a naturally-occurring acellular ECM. For example, the acellular ECM is or is derived from vitreous humour.

In one embodiment, the acellular extracellular matrix is decellularized extracellular matrix.

In one embodiment, the one or more bioactive agents are liberated by interaction of the one or more cells with the ECM, for example with the aECM or the dECM.

In one embodiment of a composition as described above comprising one or more cells, the composition comprises an homogenous population of cells. In one example, the cells are macrophages, such as activated macrophages.

In one embodiment of a composition comprising one or more cells, the composition comprises two or more populations of cells. In one example, one population comprises macrophages, and/or one population comprises fibroblasts, and/or one population comprises keratinocytes.

In one example, the one or more cells are derived from the same species as that from which the ECM is derived.

A further aspect of the present invention relates to a composition comprising one or more bioactive agents identified by a method as herein described.

In one embodiment, the one or more bioactive agents are liberated by interaction of the one or more cells with the ECM.

In a further aspect, the present invention relates to a method of mediating a biological effect in a biological sample or a subject in need thereof, the method comprising contacting the biological sample or by administering to the subject an effective amount of a protein selected from the group comprising:

a) a polypeptide comprising, consisting essentially of, or consisting of an amino acid sequence corresponding to residues 1 to 188 of mammalian Decorin;

b) a polypeptide comprising, consisting essentially of, or consisting of an amino acid sequence corresponding to residues 31 to 188 of mammalian Decorin;

c) an N-terminal fragment of mammalian Decorin comprising, consisting essentially of, or consisting of at least 10 contiguous amino acids corresponding to any amino acid sequence within residues 1 to 188 of mammalian Decorin;

d) an N-terminal fragment of mammalian Decorin comprising, consisting essentially of, or consisting of at least 10 contiguous amino acids corresponding to any amino acid sequence within residues 31 to 188 of mammalian Decorin;

e) a polypeptide comprising, consisting essentially of, or consisting of an amino acid sequence corresponding to residues 1 to 177 of mammalian Decorin;

f) a polypeptide comprising, consisting essentially of, or consisting of an amino acid sequence corresponding to residues 31 to 177 of mammalian Decorin;

g) an N-terminal fragment of mammalian Decorin comprising, consisting essentially of, or consisting of at least 10 contiguous amino acids corresponding to any amino acid sequence within residues 1 to 177 of mammalian Decorin;

h) an N-terminal fragment of mammalian Decorin comprising, consisting essentially of, or consisting of at least 10 contiguous amino acids corresponding to any amino acid sequence within residues 31 to 177 of mammalian Decorin;

i) a polypeptide comprising, consisting essentially of, or consisting of an amino acid sequence corresponding to residues 1 to 170 of mammalian Decorin;

j) a polypeptide comprising, consisting essentially of, or consisting of an amino acid sequence corresponding to residues 31 to 170 of mammalian Decorin;

k) an N-terminal fragment of mammalian Decorin comprising, consisting essentially of, or consisting of at least 10 contiguous amino acids corresponding to any amino acid sequence within residues 1 to 170 of mammalian Decorin;

l) an N-terminal fragment of mammalian Decorin comprising, consisting essentially of, or consisting of at least 10 contiguous amino acids corresponding to any amino acid sequence within residues 31 to 170 of mammalian Decorin;

m) a polypeptide comprising, consisting essentially of, or consisting of the amino acid sequence depicted in any one of Sequence ID Nos: 1 to 4;

n) a polypeptide comprising, consisting essentially of, or consisting of at least about 10 contiguous amino acids from any one of a) to m) above;

o) a polypeptide comprising or consisting of at least about 10 contiguous amino acids from any one of a) to n) above, wherein said polypeptide comprises a motif or region capable of interacting with or recruiting one or more cells, including one or more stem cells; and p) a polypeptide comprising or consisting of at least about 10 contiguous amino acids from any one of a) to o) above, wherein said polypeptide comprises a motif or region capable of interacting with or recruiting one or more mesenchymal stem cells;

q) a functional fragment, a functional variant, a peptide analogue or peptidomimetic, or a derivative of any one of a) to p) above; and r) a polypeptide having at least about 70% amino acid identity to any one of a) to q) above.

s) any combination of any two or more of a) to r) above.

In one embodiment, the biological effect is mediated in vivo in a subject in need thereof, for example by administration of the protein to the subject. In one embodiment, the effective amount is a therapeutically effective amount.

In another embodiment, the biological effect is mediated ex vivo, for example, in vitro, for example by contacting a biological sample with the protein. For example, the biological effect is mediated in vitro by contacting one or more cells, one or more tissues, or one or more organs with the protein.

In another aspect, the invention relates to a method of modulating tissue repair in a subject in need thereof, the method comprising administering to the subject a therapeutically effective amount of a protein as described herein.

In certain embodiments, the therapeutically effective amount is sufficient to recruit one or more stem cells, for example, to the site of administration, or to the site at which the administered protein is localised.

In a further aspect, the invention relates to a method of treating a disease or disorder associated with a stem cell deficiency in a subject in need thereof, the method comprising administering to the subject a therapeutically effective amount of a protein as described herein.

In one embodiment, the disease or disorder is a disease or disorder associated with a localised stem cell deficiency, such as a stem cell deficiency in a particular tissue or organ.

In still another aspect, the invention relates to a method of modulating stem cell recruitment or a related process in a subject in need thereof, the method comprising administering to the subject a therapeutically effective amount of a protein as described herein.

In various embodiments, the related process is angiogenesis, hematopoiesis, protein expression, induction, or deposition, tissue remodelling, repair, or regeneration, cellular proliferation, cellular differentiation including stem cell differentiation, cellular regulation, apoptosis, modulation of one or more immune responses, modulation of tumourigenesis, chemotaxis, or cell recruitment.

In still another aspect, the invention relates to a method of mediating a biological effect, of modulating tissue repair in a subject in need thereof, of treating a disease or disorder associated with a stem cell deficiency in a subject in need thereof, or of modulating stem cell recruitment or a related process in a subject in need thereof, the method comprising administering to the subject a therapeutically effective amount of a pharmaceutically acceptable composition as described herein.

In still another aspect, the invention relates to a method of mediating a biological effect, of modulating tissue repair in a subject in need thereof, of treating a disease or disorder associated with a stem cell deficiency in a subject in need thereof, or of modulating stem cell recruitment or a related process in a subject in need thereof, the method comprising administering to the subject a therapeutically effective amount of a bioactive agent identified in a method as described herein.

In various embodiments, the polypeptide described herein is administered to the subject at a dosage of from about 1 ng/kg to about 1 mg/kg. For example, the polypeptide described herein is administered at a dosage of from about 1 ng/kg to about 100 μg/kg, or from about 1 ng/kg to about 10 μg/kg, 1 ng/kg to about 1 μg/kg, or from about 1 ng/kg to about 100 ng/kg.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7). These are only examples of what is specifically intended and all possible combinations of numerical values between the lowest value and the highest value enumerated are to be considered to be expressly stated in this application in a similar manner.

Those skilled in the art will appreciate the meaning of various terms of degree used herein. For example, as used herein in the context of referring to an amount (e.g., "about 9%"), the term "about" represents an amount close to and including the stated amount that still performs a desired function or achieves a desired result, e.g. "about 9%" can include 9% and amounts close to 9% that still perform a desired function or achieve a desired result. For example, the term "about" can refer to an amount that is within less than 10% of, within less than 5% of, within less than 1% of, within less than 0.1% of, or within less than 0.01% of the stated amount. It is also intended that where the term "about" is used, for example with reference to a figure, concentration, amount, integer or value, the exact figure, concentration, amount, integer or value is also specifically contemplated.

Other objects, aspects, features and advantages of the present invention will become apparent from the following description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

FIG. 6 presents two representations of the sequence of ovine DCN (1-360; accession number: Q9TTE2) (grey) as discussed herein in Example 4. FIG. 6A shows the location of the peptide fragments identified by ESI MS/MS, including the putative MayDay(31-189) sequence (grey underlined), and the DCN peptide fragments identified from ESI analysis derived from samples of trypsin digested media ('blue'), size exclusion ('yellow') and Tris-Tricine in-gel digestion ('green'). FIG. 6B shows the putative MayDay (31-188) sequence (grey underlined), together with the location of protease cleavage sites predicted by MEROPS based on the human DCN sequence (1-360; accession number: P07585). Cleavage sites on the DCN sequence are indicated as 'bold' text; '↑' indicates the predicted C-terminal residue of the cleave site for each indicated protease.

FIG. 9 shows the in vivo bioactivity of recombinant MayDay peptide in recruiting MSCs in a whole animal model, as described in Example 7.

DETAILED DESCRIPTION

Figure 1:
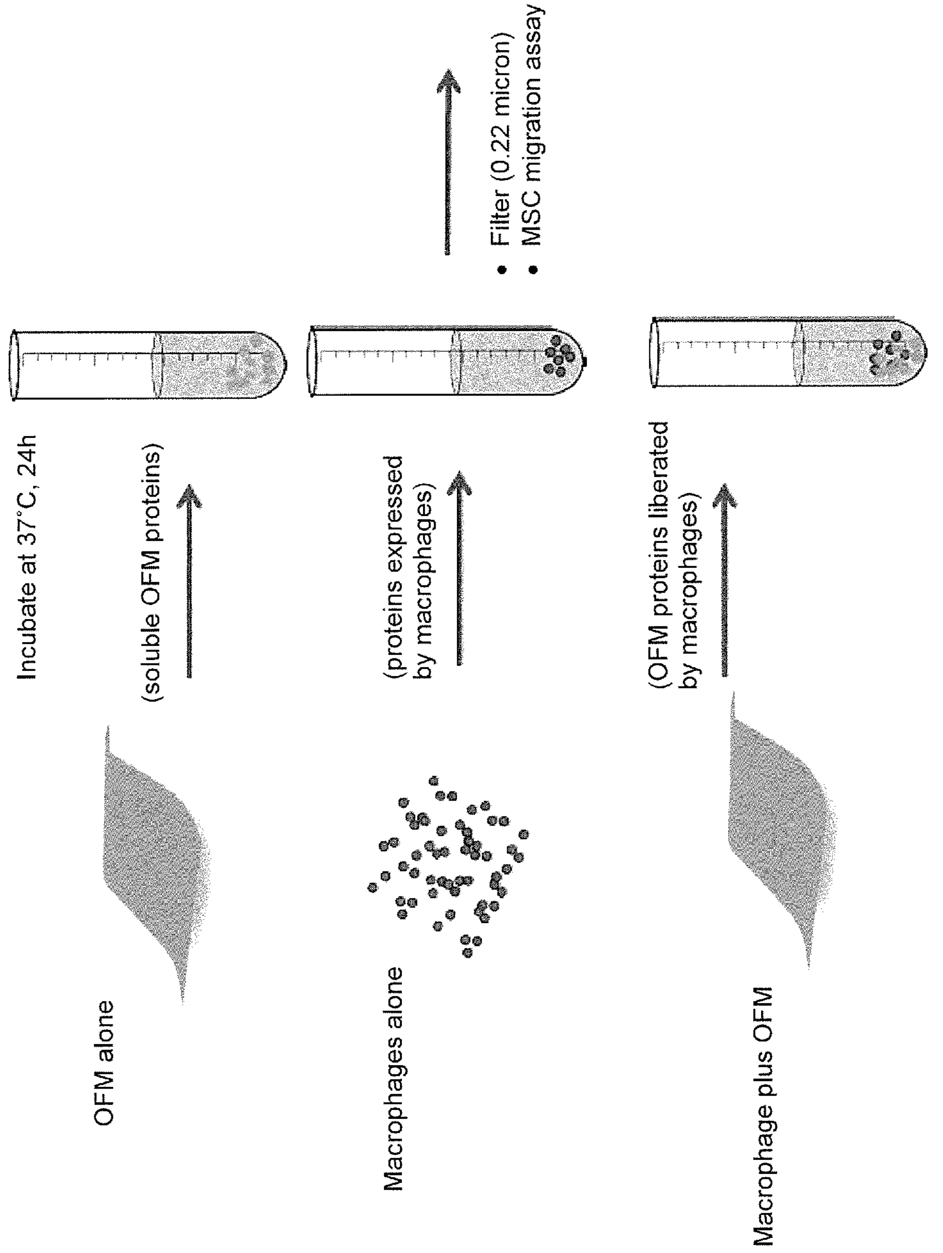
FIG. 1 shows a schematic of a representative analytical methodology as described herein, utilizing a co-culture of mammalian cells with a tissue-derived dECM. The cells modify, liberate or process components of the dECM to generate bioactive agents, such as bioactive agents with therapeutic properties suitable for the treatment of human disease, which are then assessed for bioactivity.
Figure 2:
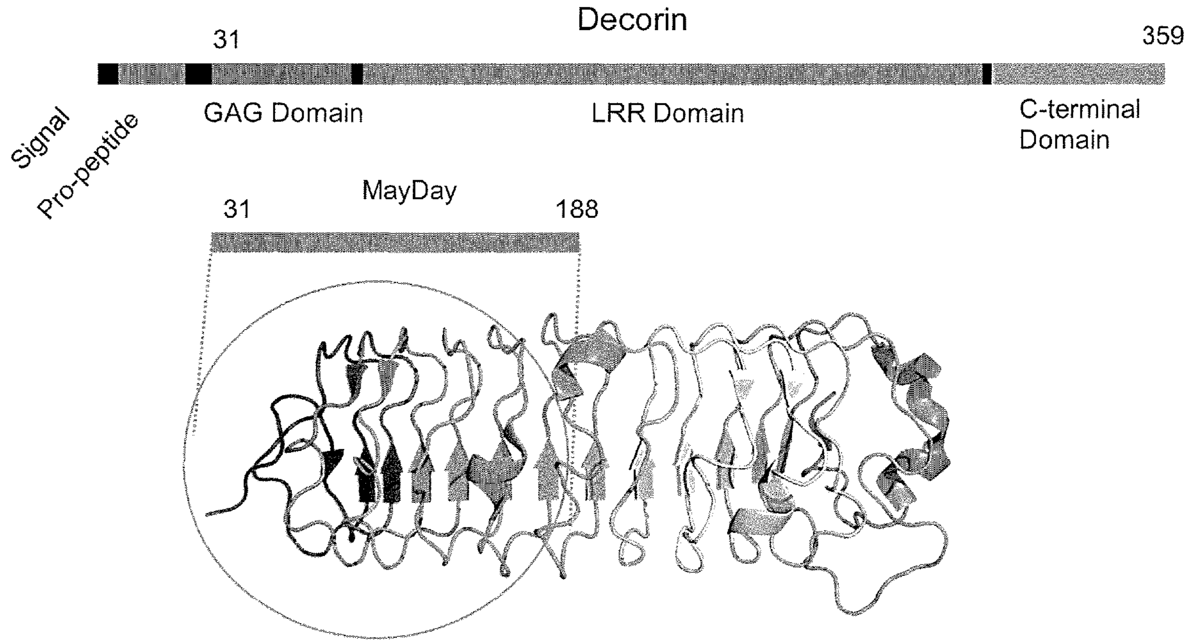
FIG. 2 shows the secondary structure and functional domains of full length ovine Decorin, along with the location of the MayDay polypeptide, and the X-ray crystal structure of Decorin.

The present invention relates to methods for the identification of one or more bioactive agents, including therapeutic agents, produced during or liberated by the interaction of one or more cells with acellular ECM. In certain embodiments, the one or more bioactive agents originate from tissue ECM, for example where the agent is a component of the ECM, a fragment of a component of the ECM, or a component or fragment of the ECM that has been modified, for example by the interaction of the one or more cells with the ECM, and which is therefore different from the form it has in native ECM.

In other embodiments, the one or more bioactive agents are produced, secreted or expressed by one or more of the cells as a result of their interaction with the acellular ECM.

As used herein, a "bioactive agent" is an agent capable of eliciting a biological response, for example, are capable of stimulating a biological response in one or more cells, or indeed in one more tissues, organs, or organisms. Particularly contemplated bioactive agents are those produced by a biological system or in response to a biological interaction or stimulus, and thus are themselves biological in character. For example, as contemplated herein, a bioactive agent is in certain embodiments a protein or polypeptide, a lipid, a polysaccharide, a nucleic acid, a chemokine, a vitamin, a hormone, a metabolite, a growth factor, a cytokine, an exosome, and the like. Particularly contemplate bioactive agents are those that elicit a biological response, for example, elicit one or more of cellular chemotaxis and/or recruitment, tissue remodelling and/or modulation of tissue repair, wound healing and/or regeneration, the modulation of immune responses, the modulation of angiogenesis, the modulation of tissue microenvironments, angiogenesis, hematopoeisis, protein expression, induction, or deposition, cellular proliferation, cellular differentiation including stem cell differentiation, cellular regulation including cell cycle regulation, apoptosis, modulation of one or more immune responses, and modulation of tumourigenesis.

Those skilled in the art will recognise, on reading this description, that various uses of and for these bioactive agents, particularly in research and therapeutic methods involving cellular chemotaxis and recruitment, such as tissue remodelling, modulation of tissue repair and wound healing, the modulation of immune responses, the modulation of angiogenesis, and the modulation of tissue microenvironments, for example, are provided.

Various aspects of the invention are described in further detail in the following subsections. Unless otherwise defined, all technical and scientific terms used herein have the same meaning as is commonly understood by one of ordinary skill in the art to which this invention belongs. In case of conflict, the present specification, including definitions, will control. Although methods and materials similar or equivalent to those described herein can be used in the practice of the invention, examples of suitable methods and materials are described below. The materials, methods, and examples described herein are illustrative only and are not intended to be limiting.

Definitions

As used herein, the term "and/or" can mean "and" or "or".

The terms "comprise", "comprises", and "comprising" as used in this specification and claims are not to be interpreted in an exclusive or exhaustive sense, and mean "consisting at least in part of". When interpreting each statement in this specification that includes the term "comprise", "comprises", or "comprising", features other than that or those prefaced by the term may also be present. Related terms such as "including", "include" and "includes" are to be interpreted in the same manner.

The term "consisting essentially of" when used in this specification refers to the features stated and allows for the presence of other features that do not materially alter the basic characteristics of the features specified.

The term "consisting of" as used herein means the specified materials or steps of the claimed invention, excluding any element, step, or ingredient not specified in the claim.

ECM

ECM biomaterials suitable for use herein are collagen-based biodegradable matrices comprising highly conserved collagens, glycoproteins, proteoglycans and glycosaminoglycans in their natural configuration and natural concentration.

One extracellular collagenous matrix for use in this invention is ECM of a warm-blooded vertebrate. ECM can be obtained from various sources, for example, intestinal tissue harvested from animals raised for meat production, including pigs, cattle and sheep or other warm blooded vertebrates. Vertebrate ECM is a plentiful by-product of commercial meat production operations and is thus a low cost tissue graft material.

The ECM biomaterial comprises naturally associated ECM proteins, glycoproteins and other factors that are found naturally within the ECM depending upon the source of the ECM.

In certain embodiments contemplated herein, the ECM utilised in accordance with this disclosure is acellular ECM (aECM)—that is, tissue ECM that is substantially free of cells.

In various embodiments, the aECM useful herein is a naturally-occurring aECM—that is, an ECM that is substantially free of cells in vivo. Examples include vitreous humour ECM from, for example, mammalian, reptilian, or avian eyes.

In other embodiments, the ECM is derived from ECM that is associated with one or more cells in vivo, but from which substantially all of the cells have been removed. Herein, ECM that has been decellularised, whether by active manipulation in, for example, a laboratory, or by other processing, is generally referred to as decellularized ECM (dECM).

Thus, in certain embodiments contemplated herein, the ECM found in tissue is decellularized to isolate or partially purify the ECM. These types of materials are widely used in wound care and soft tissue regeneration, typically as a scaffold to temporarily replace missing or damaged ECM in the patient. As the dECM mimics the tissue ECM, cells of the patient will attach to the exogenous dECM, grow and divide. Over time, the dECM will be incorporated in the patient's new tissue. It has been reported that dECM will interact with the patient's cells during regeneration via processes that mimic normal cell-ECM interactions. For example, it is reported that dECM stimulates vascularization in the new tissue and undergo constructive remodeling. As with ECM found in tissues, these dECMs contain a heterogenous mixture of structural, adhesion and signaling molecules.

ECM may be obtained from any suitable source, for example sheep forestomach. Typically, the ECM will be decellularized so such that the host cells are reduced or removed entirely.

Forestomach tissue is a preferred source of ECM for use in this invention. Suitable forestomach ECM typically comprises the propria-submucosa of the forestomach of a ruminant. In particular embodiments of the invention, the propria-submucosa is from the rumen, the reticulum or the omasum of the forestomach. These tissue scaffolds typically have a contoured luminal surface. The ECM tissue scaffold may additionally contain decellularized tissue, including portions of the epithelium, basement membrane or tunica muscularis, and combinations thereof. The tissue scaffolds may also comprise one or more fibrillar proteins, including but not limited to collagen I, collagen III or elastin, and combinations thereof.

In one particularly contemplated example, dECM is prepared from ovine forestomach tissue using processes to remove the residual ovine (sheep) cells and disinfect the resultant ECM. This dECM is referred to herein as "ovine forestomach matrix" (OFM). The term "ovine forestomach matrix" and the abbreviation OFM, as used herein, refers to an ECM scaffold containing the propria-submucosa of the forestomach of a ruminant. The term "propria-submucosa," as used herein, refers to the tissue structure formed by the blending of the lamina propria and submucosa in the ruminant forestomach.OFM has been shown to contain various components of tissue ECM, to stimulate blood vessel formation and to undergoe constructive remodeling.

The ECM useful herein will usually be amenable to easy handling, amenable to drying such as freeze-drying, and amenable to ready sterilization.

In various embodiments, the ECM is from human or animal tissue source, such as ovine, bovine, porcine, caprine, cervine, or human tissue. For example, the ECM is or comprises human dECM, ovine dECM, bovine dECM, porcine dECM, cervine dECM, or caprine dECM.

In one embodiment, the ECM is from foetal or neonatal tissue. In another embodiment, the ECM is from juvenile, adult, or elderly tissue.

In one embodiment, the ECM is from healthy tissue. In other embodiments, the ECM is from diseased tissue, such as ECM from cancerous tissue.

In one embodiment, the ECM is from whole organ or from a specific tissue, for example, the ECM is from liver, kidney, lung, intestine, amnion membrane, nerve, skin, or blood vessel tissue.

In a particularly contemplated embodiment, the ECM is from the forestomach of a ruminant. In certain embodiments, the ECM is from the rumen, the reticulum, or the omasum of the forestomach. The ECM will in certain embodiments comprise portions of the epithelium, basement membrane, or tunica muscularis, and combinations thereof, from such tissues.

In various embodiments, the ECM comprises one or more fibrillar proteins, including but not limited to collagen I, collagen III, or elastin, and combinations thereof.

It will be appreciated that in certain embodiments of the methods described herein, dECM derived from a specific tissue is contacted with one or more cells from or associated with that tissue in vivo. However, in other embodiments, dECM derived from a specific tissue is contacted with one or more cells not usually in or associated with that tissue in vivo. For example, ECM from the intestine is in one such embodiment contacted with keratinocytes isolated from mammalian skin.

While embodiments of the methods described herein in which ECM substantially free of cells and also substantially free of other material is employed are specifically contemplated, it will be appreciated that in other embodiments, the ECM may be associated with other materials, such as one or more structural supports, including for example one or more polymeric sheets. In the context of the identification methods described herein, it will be appreciated that any other materials present when the ECM is contacted with the one or more cells will ideally be biologically inert and/or incapable of influencing an interaction of the one or more cells with the ECM. Representative examples of polymers useful in providing structural support to the ECM include polyvinyl alcohol, poly-glycolic acid (PGA), poly-lactic acid (PLA), poly-lactic co-lactic acid (PLLA), and poly(lactic acid)-poly (glycolic acid) (PLGA) polymers.

Methods to Decellularize ECM

The methods described herein benefit from the use of ECM substantially free of cells.

Those skilled in the art will be familiar with surgical methods appropriate to isolating ECM and preparing it for subsequent use, including those appropriate to isolating aECM from suitable tissues in or from a subject animal. Methods to decellularize ECM are well known in the art—see, for example, U.S. Pat. Nos. 4,902,508, 5,554,389, 6,099,567 and 8,415,159, each incorporated by reference herein in its entirety.

In one embodiment, ECM suitable for use as herein described is prepared by transmural osmotic flow across the wall of an organ, such as a ruminant forestomach. Generally, an organ is filled with one solution, sealed and then immersed in another solution. The difference in salinity between the two solutions results in a transmural osmotic flow. It will be appreciated that an osmotic gradient can be established in either direction by changing the placement of the solutions (i.e., hypertonic and hypotonic solutions). The gradient is preferably established in a direction mimicking the natural flow of the organ. For example, when processing tissue from the forestomach of a ruminant, the gradient is preferably established from the luminal to the abluminal surface of the tissue.

Exemplary methods for decellularization of ECM by transmural osmotic flow are presented in PCT International patent application PCT/NZ2009/000152, published as WO2010/014021, and in U.S. Pat. No. 8,415,159, each incorporated herein by reference in its entirety.

Briefly, a segment of the vertebrate forestomach, preferably harvested from ovine species is subjected to a transmural osmotic flow between two sides of the tissue, such that the tissue layers within all or a portion of the tissue are separated and/or decellularized. The transmural osmotic flow is directed from the luminal to the abluminal side of all or a portion of the tissue, or from the abluminal to the luminal side of all or a portion of the tissue. This may be achieved, for example, by separating the tissue between a hypertonic and a hypotonic solution, such that the transmural osmotic flow is directed from the hypotonic solution to the hypertonic solution.

The method will in certain embodiments further involve removing all or part of a tissue layer including epithelium, basement membrane, or tunica muscularis, and combinations thereof.

The hypertonic and hypotonic solutions will usually include, for example, water and optionally at least one buffer, detergent or salt. The hypertonic solution contains a higher concentration of solute than the hypotonic solution. In a particular method, the hypertonic solution comprises 4 M NaCl and the hypotonic solution comprises 0.28% Triton X-200 and 0.1% EDTA. In another particular method, the hypotonic solution comprises 0.1% SDS. In still another method, the hypotonic solution comprises 0.028% Triton X-200, 0.1% EDTA, and 0.1% SDS.

The ECM can be stored in a hydrated or dehydrated state. Lyophilized or air dried ECM may be rehydrated or partially rehydrated and used in accordance with this invention without significant loss of its biotropic and mechanical properties.

It will be evident from this disclosure that the term "decellularised" as used herein refers to the removal of cells and their related debris from a portion of a tissue or organ, for example, from ECM.

It will also be apparent from this disclosure that the term "decellularized extracellular matrix" (dECM) as used herein refers to animal or human tissue that has been decellularized, and provides a matrix for structural integrity and a framework for interacting with or for carrying other materials.

Cells Suitable for Use in the Methods Herein

It will be appreciated by those skilled in the art that effectively all tissue cells, including fibroblasts, immune cells (for example, macrophages, neutrophils, and dendritic cells), endothelial cells, and stem cells (e.g. mesenchymal stem cells and progenitor cells) interact continuously in vivo with the ECM, for example via various signalling pathways, ECM adhesion molecules and receptors. For example, fibroblast cells synthesize collagen and other ECM proteins that then assemble into fibers. The fibroblast cells remain intimately involved in controlling fiber contraction and matrix stiffness in a continuous feedback loop. Other cells are also involved in the degradation and re-assembly of the matrix. For example, inflammatory cells such as macrophages and mast cells release proteases to breakdown the matrix after injury. Similarly, infiltrating endothelial cells, keratinocytes and fibroblasts release proteases to facilitate tissue remodelling, while numerous cytokines and growth factors are involved in important wound healing processes including angiogenesis, chemotaxis, proliferation, collagen synthesis and inflammation.

In one embodiment, the one or more cells contacted in vitro with aECM is or comprises any animal cell. For example, the cell is a mammalian cell. In another example, the cell is any tissue cell.

In one embodiment, the one or more cells is any eukaryotic or prokaryotic cell, for example, a plant cell, a bacterial cell, a fungal cell including a yeast cell.

In one embodiment, the one or more cells is or comprises a cell from an immortalized cell line or from a primary cell line.

In one embodiment, the one or more cells is or comprises a mixture of cells from a single tissue, such as peripheral blood mononuclear cells (PMNCs).

In one embodiment, the one or more cells is or comprises a mixture of different cells, whether from a single tissue, such as epidermal cells and keratinocytes from skin, or from multiple tissues, such as bone marrow derived stem cells and blood-derived macrophages.

In various embodiments, the one or more cells is or has been subject to stress or to one or more specific culture conditions, such as low oxygen partial pressure, nutrient depletion, altered pH, specific media, elevated $CO_2$, microorganism or viral challenge, and the like.

In various embodiments, the one or more cells are or have been induced to take a particular phenotype, such as an M1- or M2-macrophage phenotype, such as that induced by the addition of cytokines or LPS.

In various embodiments, the one or more cells are or have been genetically modified, such as genetically modified or induced to express one or more specific proteins, or comprise one or more genetic mutations.

In various embodiments, the ratio of cells to the surface area of the ECM can range from 1000 cells/cm$^2$ to 1,000,000 cells/cm$^2$, but will usually be in the order of about 100,000 cells/cm$^2$. The co-culture is incubated under controlled temperature and humidity for a period of from 1 hour to 7 days or more. In certain examples, the period is at least about 6 hours, at least about 12 hours, at least about 18 hours, or at least about 24 hours.

In one specifically contemplated embodiment, macrophage cells are cultured on OFM, for instance as exemplified herein in the Examples.

Identification of Bioactives

The detection and/or identification of the one or more bioactive agents as contemplated herein will in certain embodiments utilize modern chromatographic separation techniques (e.g. size exclusion chromatography, gel electrophoresis or fast protein high pressure liquid chromatography) to separate a starting material, such as a sample recovered following the interaction of the one or more cells with the aECM, into various fractions.

In certain embodiments, these fractions are assayed using an appropriate model of the biology of interest. With successive rounds of isolation and purification the therapeutic agent can be identified, based on biological activity of the fraction.

In certain embodiments, the detection and/or identification of one or more of the bioactive agents, such as one or more bioactive polypeptides described herein, involves the direct detection of the bioactive agent itself. In certain embodiments such detection is by detection methods well known in the art, such as mass spectrometry, HPLC, 2D SDS-PAGE, or antibody binding. Exemplary methods for such detection are presented herein, and are readily amenable to rapid screening of samples.

In certain embodiments, detection and/or identification utilises one or more antibodies capable of selectively and specifically binding one or more of the bioactive agents, such as one or more bioactive proteins described herein. In certain embodiments of the detection or diagnostic methods described herein, antigen-antibody binding is detected using immunoassay. The design of the immunoassay may vary. For example, the immunoassay may be based upon competition or direct reaction. Furthermore, protocols may use solid supports or may use cellular or extracellular material. The detection of the antibody-antigen complex may involve the use of labelled antibodies, including labelled secondary antibodies. In various embodiments the labels may be, for example, enzymes, fluorescent-, chemoluminescent-, radioactive- or dye molecule labels.

The immunoassay may include various formats, for example chip-based immunoassay, enzyme-linked immunosorbent assay (ELISA), flow-through (vertical flow) test or lateral flow assay, immunofluorescence test (IFT), or Western blot analysis.

In certain embodiments, the detection of one or more of the bioactive agents, such as one or more bioactive polypeptides described herein, involves the detection of one or more biological effects mediated by the bioactive agent. Representative examples exemplified herein include the recruitment of one or more cells in an in vitro assay of cellular chemotaxis. Many assays of various biological effects and/or responses are known to those skilled in the art. Examples include cell proliferation assays, including assays of fibroblast proliferation or keratinocyte proliferation; cell migration assays, including assays of endothelial cell migration, mesenchymal stem cell migration, fibroblast migration, keratinocyte migration; cell differentiation assays, including assays of progenitor cells derived from nerve tissue, bone marrow cells, chondrocytes (including osteogenesis, chondrogenesis, etc.); cellular polarization assays, such as assays of macrophage polarization; immune cell activation assays, including neutrophil activation assays, mast cell activation assays, T cell activation assays, B cell activation assays including antibody production assays; assays of phagocytosis, including neutrophil phagocytosis assays, macrophage phagocytosis assays, and mast cell phagocytosis assays; cell apoptosis assays, for example tumour cell apoptosis assays, and endothelial cell apoptosis assays; antibacterial, antifungal, and antiviral assays; and assays of angiogenesis, including assays of endothelial cell migration and endothelial cell sprouting assays.

Bioactive Agents

Proteins present in or derived from ECM, including altered or fragmented proteins and peptides, such as those produced through proteolytic activity engendered by one or more cells, are examples of the bioactive agents amenable to identification, isolation, and use according to this disclosure.

In one example, the protein is a protein selected from the group comprising:

a) a polypeptide comprising, consisting essentially of, or consisting of an amino acid sequence corresponding to residues 1 to 188 of mammalian Decorin;
b) a polypeptide comprising, consisting essentially of, or consisting of an amino acid sequence corresponding to residues 31 to 188 of mammalian Decorin;
c) an N-terminal fragment of mammalian Decorin comprising, consisting essentially of, or consisting of at least 10 contiguous amino acids corresponding to any amino acid sequence within residues 1 to 188 of mammalian Decorin;
d) an N-terminal fragment of mammalian Decorin comprising, consisting essentially of, or consisting of at least 10 contiguous amino acids corresponding to any amino acid sequence within residues 31 to 188 of mammalian Decorin;
e) a polypeptide comprising, consisting essentially of, or consisting of an amino acid sequence corresponding to residues 1 to 177 of mammalian Decorin;
f) a polypeptide comprising, consisting essentially of, or consisting of an amino acid sequence corresponding to residues 31 to 177 of mammalian Decorin;
g) an N-terminal fragment of mammalian Decorin comprising, consisting essentially of, or consisting of at least 10 contiguous amino acids corresponding to any amino acid sequence within residues 1 to 177 of mammalian Decorin;
h) an N-terminal fragment of mammalian Decorin comprising, consisting essentially of, or consisting of at least 10 contiguous amino acids corresponding to any amino acid sequence within residues 31 to 177 of mammalian Decorin;
i) a polypeptide comprising, consisting essentially of, or consisting of an amino acid sequence corresponding to residues 1 to 170 of mammalian Decorin;
j) a polypeptide comprising, consisting essentially of, or consisting of an amino acid sequence corresponding to residues 31 to 170 of mammalian Decorin;
k) an N-terminal fragment of mammalian Decorin comprising, consisting essentially of, or consisting of at least 10 contiguous amino acids corresponding to any amino acid sequence within residues 1 to 170 of mammalian Decorin;
l) an N-terminal fragment of mammalian Decorin comprising, consisting essentially of, or consisting of at least 10 contiguous amino acids corresponding to any amino acid sequence within residues 31 to 170 of mammalian Decorin;
m) a polypeptide comprising, consisting essentially of, or consisting of the amino acid sequence depicted in any one of Sequence ID Nos: 1 to 4;
n) a polypeptide comprising, consisting essentially of, or consisting of at least about 10 contiguous amino acids from any one of a) to m) above;
o) a polypeptide comprising or consisting of at least about 10 contiguous amino acids from any one of a) to n) above, wherein said polypeptide comprises a motif or region capable of interacting with or recruiting one or more cells, including one or more stem cells; and p) a polypeptide comprising or consisting of at least about 10 contiguous amino acids from any one of a) to o) above, wherein said polypeptide comprises a motif or region capable of interacting with or recruiting one or more mesenchymal stem cells;

q) a functional fragment, a functional variant, a peptide analogue or peptidomimetic, or a derivative of any one of a) to p) above; and r) a polypeptide having at least about 70% amino acid identity to any one of a) to q) above.

In other examples, the bioactive agent is a matrikine, a matricryptins, a subdomain of an ECM protein, or a ligand present in or derived from an ECM protein.

Proteins present in or derived from ECM, including altered or fragmented proteins and peptides, such as those produced through proteolytic activity, have been reported to be involved in a number of processes, including tissue remodelling, angiogenesis, and cell proliferation. Examples of such proteins include so-called matrikines and matricryptins, being polypeptides derived from or comprising subdomains of ECM proteins and which are capable of modulating cell signalling.

Matrikines are specific regions of ECM proteins which act as ligands and alter cell behavior after ligand-receptor binding. For example, the discoidin domain receptor (DDR) binding sequence of collagen is a well characterized matrikine (Bellon, Martiny et al. 2004, Maquart, Pasco et al. 2004, Tran, Lamb et al. 2005). The binding of this ligand to the receptor DDR-1 in epithelial cells reportedly leads to smooth muscle cell migration. Binding of the same consensus to the receptor DDR-2 in mesenchymal stem cells (MSC) reportedly induces the production of MMP-1, leading to the degradation of nearby fibrillary collagen.

In contrast, matricryptins are ligands that must be released from their parent proteins, for example by proteolytic cleavage, cellular processing or after a conformational change in the parent protein, to elicit their biological activity and/or to bind their target receptors.

It has been reported that matrikine and matricyrptin ligands often act with a lower binding affinity, in the mM range, compared with cytokines which usually act in the nM range. It has been suggested that this lower binding affinity is compensated for by the fact that the ligand can occur as a tandem repeating sequence within the parent protein, and because these ligands are not usually internalised or depleted by the target cell. In addition, as these ligands are derived from the ECM, cells within the ECM are in close proximity to their site of production and the local concentration of these ligands at cells present in the ECM can be relatively high, unlike secreted growth factors which form gradients from a distance.

Matricryptins or cryptic peptides fragments will in certain cases have a different or altered bioactive function to the parent protein from which they are derived. For example, fragments of collagen and elastin have been reported to promote migration, differentiation and proliferation of wound healing cells. The disruption of the basement membrane also reportedly breaks adhesion molecules between keratinocytes and proteins such as fibronectin, collagen IV and laminin, activating the keratinocytes. The breakdown of the provisional matrix proteins, especially GAGs and proteoglycans, has been reported to release signaling molecules which alter fibroplasia, angiogenesis and also the inflammatory response. Heparin sulphate is broken down by heparinase to produce lower molecular weight fragments that promote the activity of FGF2 and degradation products of hyaluronic acid have been reported to induce angiogenesis in a chick chorioallantoic membrane (CAM) model. Matricryptin EGF-like repeats are present on laminin 5, but this ligand must be made available by the action of MT1-MMP and MMP-2 before it will apply its biological function. Other examples of matricryptins include endostatin, released from collagen XVIII by elastase, cathepsins and MMPs; tumstatin, released from collagen IV by MMP-9; and the XGXXPG consensus of elastin, released by MMP-2, MMP-9, MMP-7 and MMP-12.

Those skilled in the art will recognise, on reading this description, that these proteins can be considered representative examples of the bioactive agents able to be identified by the methods contemplated herein. As such, various uses of and for these proteins, particularly in research and therapeutic methods involving cellular chemotaxis and recruitment, such as tissue remodelling, modulation of tissue repair and wound healing, the modulation of immune responses, the modulation of angiogenesis, and the modulation of tissue microenvironments, for example, are provided.

Proteins suitable for use herein include naturally-occurring proteins and peptides, and derivatives thereof including proteins and peptides having one or more amino acid variations from a naturally-occurring protein or peptide.

The term "amino acid" refers to natural amino acids, non-natural amino acids, and amino acid analogues. Unless otherwise indicated, the term "amino acid" includes both D and L stereoisomers if the respective structure allows such stereoisomeric forms.

Natural amino acids include alanine (Ala or A), arginine (Arg or R), asparagine (Asn or N), aspartic acid (Asp or D), cysteine (Cys or C), glutamine (Gin or Q), glutamic acid (Glu or E), glycine (Gly or G), histidine (His or H), isoleucine (He or I), leucine (Leu or L), Lysine (Lys or K), methionine (Met or M), phenylalanine (Phe or F), proline (Pro or P), serine (Ser or S), threonine (Thr or T), tryptophan (Tip or W), tyrosine (Tyr or Y) and valine (Val or V).

Non-natural amino acids include, but are not limited to, azetidinecarboxylic acid, 2-aminoadipic acid, 3-aminoadipic acid, beta-alanine, naphthylalanine ("naph"), aminopropionic acid, 2-aminobutyric acid, 4-aminobutyric acid, 6-aminocaproic acid, 2-aminoheptanoic acid, 2-aminoisobutyric acid, 3-aminoisbutyric acid, 2-aminopimelic acid, tertiary-butylglycine ("tBuG"), 2,4-diaminoisobutyric acid, desmosine, 2,2'-diaminopimelic acid, 2,3-diaminopropionic acid, N-ethyl glycine, N-ethylasparagine, homoproline ("hPro" or "homoP"), hydroxylysine, allo-hydroxylysine, 3-hydroxyproline ("3Hyp"), 4-hydroxyproline ("4Hyp"), isodesmosine, allo-isoleucine, N-methylalanine ("MeAla" or "Nime"), Nalkylglycine ("NAG") including N-methylglycine, N-methylisoleucine, N-alkylpentylglycine ("NAPG") including N-methylpentylglycine. N-methylvaline, naphthylalanine, norvaline ("Norval"), norleucine ("Norleu"), octylglycine ("OctG"), ornithine ("Orn"), pentylglycine ("pG" or "PGly"), pipecolic acid, thioproline ("ThioP" or "tPro"), homoLysine ("hLys"), and homoArginine ("hArg").

The term "amino acid analogue" refers to a natural or non-natural amino acid where one or more of the C-terminal carboxy group, the N-terminal amino group and side-chain functional group has been chemically blocked, reversibly or irreversibly, or otherwise modified to another functional group. For example, aspartic acid-(beta-methyl ester) is an amino acid analogue of aspartic acid; N-ethylglycine is an amino acid analogue of glycine; or alanine carboxamide is an amino acid analogue of alanine. Other amino acid analogues include methionine sulfoxide, methionine sulfone, S-(carboxymethyl)-cysteine, S-(carboxymethyl) cysteine sulfoxide and S-(carboxymethyl)-cysteine sulfone.

The term "expression construct" refers to a genetic construct that includes elements that permit transcribing the polynucleotide molecule of interest, and, optionally, translating the transcript into a polypeptide. An expression construct typically comprises in a 5' to 3' direction:

(1) a promoter, functional in the host cell into which the construct will be introduced, (2) the polynucleotide to be expressed, and (3) a terminator functional in the host cell into which the construct will be introduced.

Expression constructs of the invention are inserted into a replicable vector for cloning or for expression, or are incorporated into the host genome.

The term "vector" as used herein refers to a polynucleotide molecule, usually but not limited to a double stranded DNA, which is amenable to use in molecular biological techniques, for example to modify, manipulate, replicate, amplify, or transport a polynucleotide molecule. In certain embodiments, a vector is used to transport a polynucleotide molecule, such as but not limited to a genetic construct, for example an expression construct, into a host cell or organism. In certain examples the vector is capable of replication and/or maintenance in more than one host system.

A "fragment" of a polypeptide is a subsequence of the polypeptide, typically one that performs a function that is required for activity, such as enzymatic or binding activity, and/or provides a three dimensional structure of the polypeptide or a part thereof, such as an epitope. It will be appreciated that a fragment of a polypeptide may possess or elicit a different function or functions from that possessed or exhibited by the full-length polypeptide from which it is derived.

As used herein, the term "peptide" refers a short polymer of amino acids linked together by peptide bonds. While it will be recognised that the names associated with various classes of amino acid polymers (e.g., peptides, proteins, polypeptides, etc.) are somewhat arbitrary, peptides are generally of about 50 amino acids or less in length. A peptide can comprise natural amino acids, non-natural amino acids, amino acid analogues, and/or modified amino acids. A peptide can be a subsequence of naturally occurring protein or a non-natural, including a synthetic, sequence.

As used herein, the term "synthetic peptide" encompasses a peptide having a distinct amino acid sequence from those found in natural peptides and/or proteins. A "synthetic peptide," as used herein, can be produced or synthesized by any suitable method (e.g., recombinant expression, chemical synthesis, enzymatic synthesis, etc.), and can include any chemical modification to a parent peptide, and may include, but is not limited to such methods as truncations, deletions, cyclization or non-peptidic synthetic or semi-synthetic derivatives that retain the same biological function(s) as the starting peptide. Methods of protein synthesis, such as solid state synthesis, are well known in the art.

The terms "peptide mimetic" or "peptidomimetic" refer to a peptide-like molecule that emulates a sequence derived from a protein or peptide. A peptide mimetic or peptidomimetic can contain amino acids and/or non-amino acid components. Examples of peptidomimetics include chemically modified peptides, peptoids (side groups are appended to the nitrogen atom of the peptide backbone, rather than to the α-carbons), β-peptides (amino group bonded to the β carbon rather than the α-carbon), etc. Chemical modification includes one or more modifications at amino acid side groups, α-carbon atoms, terminal amine group, or terminal carboxy group. A chemical modification can be adding chemical moieties, creating new bonds, or removing chemical moieties. Modifications at amino acid side groups include, without limitation, acylation of lysine ε-amino groups, N-alkylation of arginine, histidine, or lysine, alkylation of glutamic or aspartic carboxylic acid groups, lactam formation via cyclization of lysine ε-amino groups with glutamic or aspartic acid side group carboxyl groups, hydrocarbon "stapling" (e.g., to stabilize alpha-helix conformations), and deamidation of glutamine or asparagine. Modifications of the terminal amine group include, without limitation, the desamino, N-lower alkyl, N-di-lower alkyl, constrained alkyls (e.g. branched, cyclic, fused, adamantyl) and N-acyl modifications. Modifications of the terminal carboxy group include, without limitation, the amide, lower alkyl amide, constrained alkyls (e.g. branched, cyclic, fused, adamantyl) alkyl, dialkyl amide, and lower alkyl ester modifications. Lower alkyl is C1-C4 alkyl. Furthermore, one or more side groups, or terminal groups, can be protected by protective groups known to the ordinarily skilled peptide chemist. The a-carbon of an amino acid can be mono- or dimethylated.

It will be appreciated that any one of the proteins or peptides described herein in certain embodiments comprises one or more non-naturally occurring amino acids, one or more amino acid analogues, or is or comprises a synthetic peptide or polypeptide or a peptide mimetic. Similarly, it will be appreciated that any one of the proteins or peptides described herein will in certain embodiments be the starting point for one or more modifications, synthetic methods, or protein engineering methods to develop a peptide analogue having a desired biological activity—for example, a qualitatively similar bioactivity as the parent protein or peptide, but an effect of a quantitatively different magnitude, or indeed a different bioactivity from that elicited by the parent protein or peptide.

The term "fusion polypeptide", as used herein, refers to a polypeptide comprising two or more amino acid sequences, for example two or more polypeptide domains, fused through respective amino and carboxyl residues by a peptide linkage to form a single continuous polypeptide. It should be understood that the two or more amino acid sequences can either be directly fused or indirectly fused through their respective amino and carboxyl terminii through a linker or spacer or an additional polypeptide.

The term "polypeptide", as used herein, encompasses amino acid chains of any length but preferably at least 10 amino acids, including full-length proteins, in which amino acid residues are linked by covalent peptide bonds. Polypeptides described herein are purified natural products, or are produced partially or wholly using recombinant or synthetic techniques. The term may refer to a polypeptide, an aggregate of a polypeptide such as a dimer or other multimer, a fusion polypeptide, a polypeptide variant, or derivative thereof.

It will be understood that, for the particular polypeptides and proteins contemplated herein, natural variations can exist between individual bacterial strains. These variations may be demonstrated by (an) amino acid difference(s) in the overall sequence or by deletions, substitutions, insertions, inversions or additions of (an) amino acid(s) in said sequence. Amino acid substitutions which do not essentially alter biological and immunological activities, are well known. Amino acid replacements between related amino acids or replacements which have occurred frequently in evolution are, inter alia, Ser/Ala, Ser/Gly, Asp/Gly, Asp/Asn, Ile/Val. Other amino add substitutions include Asp/Glu, Thr/Ser, Ala/Gly, Ala/Thr, Ser/Asn, Ala/Val, Thr/Phe, Ala/Pro, Lys/Arg, Leu/Ile, Leu/Val and Ala/Glu. Based on this information, methods for rapid and sensitive protein comparison and determining the functional similarity between homologous proteins were developed. Such amino acid substitutions of the exemplary embodiments described herein, as well as variations having deletions and/or insertions are within the scope of the invention as long as the resulting proteins retain their immune reactivity. This explains why one or more proteins described herein, when isolated from different field isolates, may have identity levels below 100%, while still representing the same protein with the same immunological characteristics. Those variations in the amino acid sequence of a certain protein described herein that still provide a protein capable of reacting with an antibody specific to a protein specifically identified herein are considered as immunologically functional equivalents of the proteins identified herein, and as such do not essentially influence the immunogenicity of the protein.

When a protein is used for example for diagnostic or therapeutic purposes, for example for reacting with antibodies, or for mediating a biological effect, for example one or more of the biological functions associated with the native protein in vivo, while it can be expedient to do so it is not necessary to use the whole protein. It is also possible to use a polypeptide fragment of that protein (as such or coupled to a carrier or as a component in a fusion polypeptide, for example) or a polypeptide fragment derived from that protein or a related amino acid sequence that is capable of eliciting a desired biological effect, such as an immune response against that protein or of being recognised by an antibody specific to that protein, of mediating a cell-signalling effect, or the like. Such a polypeptide fragment may be referred to with reference to the function it possesses, such as the function it shares with the full-length protein from which it was derived. For example, a polypeptide fragment having an immunological effect may be referred to as an immunogenic fragment, where an "immunogenic fragment" is understood to be a fragment of the full-length protein that retains its capability to induce an immune response in a vertebrate host or be recognised by an antibody specific to the parent protein. Similarly, a polypeptide fragment retaining or possessing one or more biological effects elicited by the full-length protein from which it was derived, or possessing a related or different biological effect, is referred to herein as a "bioactive fragment" or a "bioactive polypeptide fragment". Likewise, a polypeptide having a biological effect, such as a polypeptide capable of stimulating a biological response in a cell or eliciting a therapeutic effect, may be referred to herein as a "bioactive fragment" or a "bioactive polypeptide fragment", or grammatical equivalents thereof.

A variety of techniques is available to identify such polypeptide fragments, as well as DNA fragments encoding such fragments. For example, in the case of immunogenic fragments, such fragments may comprise one or more determinants or epitopes. Well-established empirical and in silico methods for the detection of epitopes exist and are well known to those skilled in the art. For example, computer algorithms are able to designate specific protein fragments as the immunologically important epitopes on the basis of their sequential and/or structural agreement with epitopes that are known. The determination of these regions is typically based on a combination of the hydrophilicity criteria and secondary structural features. An immunogenic fragment (or epitope) usually has a minimal length of 6, more commonly 8 amino acids, preferably more then 8, such as 9, 10, 12, 15 or even 20 or more amino acids. The nucleic acid sequences encoding such a fragment therefore have a length of at least 18, more commonly 24 and preferably 27, 30, 36, 45 or even 60 nucleic acids.

Similarly, those skilled in the art will be aware of methods to identify bioactive fragments using various assays targeted at identifying or detecting a particular biological response. Representative methods suitable for use in the identification or detection of bioactive fragments contemplated herein are presented below, including in the Examples.

The term "variant" with reference to polypeptides encompasses naturally occurring, recombinantly, and synthetically produced polypeptides, including those comprising one or more non-natural amino acids, one or more amino acid analogues, and peptide mimetics. Variant polypeptide sequences preferably exhibit at least 50%, more preferably at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least %, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identity to a sequences of the present invention. Identity is found over a comparison window of at least 20 amino acid positions, preferably at least 50 amino acid positions, at least 100 amino acid positions, or over the entire length of a polypeptide of the invention.

Polypeptide sequence identity can be determined in the following manner. The subject polypeptide sequence is compared to a candidate polypeptide sequence using BLASTP (from the BLAST suite of programs, version 2.2.10 [October 2004]) in bl2seq, which is publicly available from NCBI (ftp://ftp.ncbi.nih.gov/blast/). The default parameters of bl2seq are utilized except that filtering of low complexity regions should be turned off.

Polypeptide sequence identity may also be calculated over the entire length of the overlap between a candidate and subject polynucleotide sequences using global sequence alignment programs. EMBOSS-needle (available at http://www.ebi.ac.uk/emboss/align/) and GAP (Huang, X. (1994) On Global Sequence Alignment. Computer Applications in the Biosciences 10, 227-235.) as discussed above are also suitable global sequence alignment programs for calculating polypeptide sequence identity.

Polypeptide variants contemplated herein also encompass those which exhibit a similarity to one or more of the specifically identified sequences that is likely to preserve the functional equivalence of those sequences and which could not reasonably be expected to have occurred by random chance. Such sequence similarity with respect to polypeptides can be determined using the publicly available bl2seq program from the BLAST suite of programs (version 2.2.10 [October 2004]) from NCBI (ftp://ftp.ncbi.nih.gov/blast/). The similarity of polypeptide sequences can be examined using the following unix command line parameters:

```
bl2seq -i peptideseq1 -j peptideseq2 -F F -p blastp
```

Variant polypeptide sequences preferably exhibit an E value of less than $1\times10^{-10}$, more preferably less than $1\times10^{-20}$, less than $1\times10^{-30}$, less than $1\times10^{-40}$, less than $1\times10^{-50}$, less than $1\times10^{-60}$, less than $1\times10^{-70}$, less than $1\times10^{-80}$, less than $1\times10^{-90}$, less than $1\times10^{-100}$, less than 1×

$10^{-110}$, less than $1\times10^{-120}$ or less than $1\times10^{-123}$ when compared with any one of the specifically identified sequences.

The parameter -F F turns off filtering of low complexity sections. The parameter -p selects the appropriate algorithm for the pair of sequences. This program finds regions of similarity between the sequences and for each such region reports an "E value" which is the expected number of times one could expect to see such a match by chance in a database of a fixed reference size containing random sequences. For small E values, much less than one, this is approximately the probability of such a random match.

Conservative substitutions of one or several amino acids of a described polypeptide sequence without significantly altering its biological activity are also included in the invention. A skilled artisan will be aware of methods for making phenotypically silent amino acid substitutions (see, e.g., Bowie et al., 1990, Science 247, 1306).

A polypeptide variant contemplated herein also encompasses that which is produced from the nucleic acid encoding a polypeptide, but differs from the wild type polypeptide in that it is processed differently such that it has an altered amino acid sequence. For example, in one embodiment a variant is produced by an alternative splicing pattern of the primary RNA transcript to that which produces a wild type polypeptide.

In other embodiments, the bioactive agent a lipid, a polysaccharide, a nucleic acid, a chemokine, a vitamin, a hormone, and the like.

Therapeutic Methods and Compositions

The methods and bioactive agents described herein are in certain embodiments used in therapeutic methods, for example, in the treatment of one or more diseases, disorders, pathologies, or conditions in a subject in need thereof.

A "subject" as used herein is an animal, usually a mammal, including a mammalian companion animal or a human. Representative companion animals include feline, equine, and canine. Representative agricultural animals include bovine, ovine, caprine, cervine, and porcine.

In will be appreciated that the various methods of therapy contemplated herein will typically embody the administration of an effective amount of the bioactive agent.

An "effective amount" is an amount sufficient to effect beneficial or desired results including clinical results. An effective amount can be administered in one or more administrations by various routes of administration. The effective amount will vary depending on, among other factors, the disease or condition indicated, the severity of the disease or condition, the age and relative health of the subject, the potency of the agent administered, the mode of administration and the treatment desired. A person skilled in the art will be able to determine appropriate dosages having regard to these any other relevant factors.

Specifically contemplated diseases, disorders, pathologies or conditions to be treated include those that would benefit from the modulation of stem cell responses in the subject.

The term "treatment", and related terms such as "treating" and "treat", as used herein relates generally to treatment, of a human or a non-human subject, in which some desired therapeutic effect is achieved. The therapeutic effect may, for example, be inhibition, reduction, amelioration, halt, or prevention of a disease or condition.

The term "stem cells" as used herein refers cells capable of self-renewal without differentiation and capability to differentiate into other cell types. The term "stem cells" will, as the context confers, encompass totipotent, pluripotent, and multipotent stem cells.

Representative stem cells particularly contemplated for use herein include stem cells that have been cultured in vitro following isolation from a tissue source containing stem cells. In one embodiment, the stem cells are mesenchymal stem cells.

Stem cells are able to differentiate into other cell types and also have capacity to self-renew without differentiation. By supplying various differentiated functional cells as required, stem cells are critical for the formation of new tissues and also the repair of damaged or diseased tissues [Li, L., & Xie, T. (2005). Stem cell niche: structure and function. Annu. Rev. Cell Dev. Biol., 21, 605-631.]. In addition to this progenitor function, stem cells also exhibit their own functionality to promote tissue regeneration and repair, for example via secretion of bioactive factors and through modulating the behavior of other cell types [Duscher, D., Barrera, J., Wong, V. W., Maan, Z. N., Whittam, A. J., Januszyk, M., & Gurtner, G. C. (2016). Stem cells in wound healing: the future of regenerative medicine? A mini-review. Gerontology, 62(2), 216-225.]. As part of normal tissue growth and repair, local endogenous stem cells carry out these functions but in circumstances of extensive tissue damage or when coinciding disease factors are present the normal endogenous stem cell population may not be sufficient [Kanji, S., & Das, H. (2017). Advances of stem cell therapeutics in cutaneous wound healing and regeneration. Mediators of inflammation, 2017.].

Stem cell therapy is recognised as having great potential in regenerative medicine, with the administration of additional stem cells demonstrating improved outcomes in a range of injury and disease states including dermal wounds [Falanga, V., Iwamoto, S., Chartier, M., Yufit, T., Butmarc, J., Kouttab, N., & Carson, P. (2007). Autologous bone marrow-derived cultured mesenchymal stem cells delivered in a fibrin spray accelerate healing in murine and human cutaneous wounds. Tissue engineering, 13(6), 1299-1312.], nervous system injury [di Summa, P. G., Kingham, P. J., Raffoul, W., Wiberg, M., Terenghi, G., & Kalbermatten, D. F. (2010). Adipose-derived stem cells enhance peripheral nerve regeneration. Journal of Plastic, Reconstructive & Aesthetic Surgery, 63(9), 1544-1552.] and myocardial infarction [Berry, M. F., Engler, A. J., Woo, Y. J., Pirolli, T. J., Bish, L. T., Jayasankar, V., & Sweeney, H. L. (2006). Mesenchymal stem cell injection after myocardial infarction improves myocardial compliance. American Journal of Physiology-Heart and Circulatory Physiology, 290(6), H2196-H2203.].

However, current stem cell administration techniques are inefficient and invasive requiring donor tissue harvesting, extraction, enrichment and re-administration of the isolated stem cell populations. As such, therapeutic agents capable of inducing localized recruitment of endogenous stem cells are of considerable utility in the treatment of conditions which benefit from the activity of stem cells.

For example, in the adult bone marrow, mesenchymal stem cells (MSCs) are a pool of regenerative cells that are capable of self-renewal and play an important role in tissue repair. Firstly, they are capable of differentiating into cells that are required at the site of injury. They support haematopoiesis by maintaining the haematopoietic stem cell niche. They release cytokines that modulate the inflammatory response and trophic factors that promote healing processes such as cell recruitment, angiogenesis and collagen synthesis. MSCs, along with fibroblasts, fibrocytes and pericytes can differentiate into myofibroblast progenitors that are stimulated by cell matrix interactions, matrix stiffness and mechanical stress to become myofibroblasts—the primary matrix producing cells in wound healing.

Bone marrow derived stem cells have also been reported to form pericytes, endothelial cells and keratinocytes. As well as being able to differentiate into the type of cells required at the site of injury, MSCs have important roles in the regulation of other wound healing cells. MSCs increase the rate of fibroblast migration, proliferation and collagen synthesis as well as endothelial cell tube formation. During the inflammatory stage of wound healing, MSCs regulate the immune response by blocking T-cell proliferation, producing IL-10 and IL-4. During the proliferation stage they release paracrine signals to recruit keratinocytes, dermal fibroblasts and other nearby stem cells. They secrete important wound healing growth factors such as keratinocyte growth factor (KGF), VEGF and PDGF. Finally, during remodelling, MSCs regulate the expression of MMPs and collagen deposition.

Accordingly, the administration of a bioactive agent able to elicit MSC recruitment to a specific site is useful in the treatment of diseases, disorders, pathologies or conditions that would benefit from the myriad of biological responses MSCs are capable of eliciting. Recruitment of other stem cell types to sites of interest will likewise have therapeutic utility.

One such bioactive agent is the MayDay peptide described herein. Accordingly, particularly contemplated herein are detection, diagnostic, research and therapeutic methods, compositions, reagents, and kits that utilise one or more of the proteins described herein.

Accordingly, the invention relates to a kit for detecting and/or identifying one or more bioactive agents, for example, via a method as described herein, wherein the kit comprises acellular ECM and optionally one or more exogeneous cells, optionally together with one or more compositions as herein described.

While in the current invention the physiological effect of MayDay or a fragment, a variant, a peptide analogue, or a derivative thereof, is to recruit to stem cells, in the broader context of soft tissue regeneration this may also invoke down-stream biological processes, including but not limited to the following; angiogenesis, vascularogenesis, tissue remodeling, concentration of circulating stem stems, and muscle tissue regeneration.

The recruitment of stem cells is broadly beneficial for soft tissue repair, and for the management or intervention in a disease, disorder or pathology relating to soft tissue, including muscle. Such injuries, diseases or pathologies may include but are not limited to marocardial infarction, tissue loss due to surgical invention or trauma, concentration of stem cells, including progenitor cells in the peripheral blood system.

In one aspect the invention relates to a pharmaceutical composition comprising an effective amount of a bioactive agent identified by a method described herein, such as an effective amount of a polypeptide described herein or a pharmaceutically acceptable salt or solvent thereof, and a pharmaceutically acceptable carrier.

The pharmaceutical compositions may comprise an effective amount of two or more agents, such as two or more peptides described herein, in combination.

Compositions suitable for the administration of bioactive agents, such as a bioactive protein, including the therapeutic administration of bioactive agents including proteins or peptides to a subject in need thereof, are known in the art.

For example, the bioactive agent, such as a polypeptide as described herein, for example the so-called MayDay peptide, or a fragment, a variant, a peptide analogue, or a derivative thereof, is in certain embodiments formulated with a pharmaceutically acceptable carrier, excipient or combined with other agents to improve bioavailability, or half-life, or potency of the bioactive, and the composition is administered to the subject.

The term "pharmaceutically acceptable carrier" refers to a carrier (adjuvant or vehicle) that may be administered to a subject together with the bioactive agent, such as the MayDay peptide described herein, or a pharmaceutically acceptable salt or solvate thereof.

Once such carrier is saline (0.9% sodium chloride), though other carriers are applicable.

Pharmaceutically acceptable carriers that may be used in the compositions include, but are not limited to, ion exchangers, alumina, aluminum stearate, lecithin, self-emulsifying drug delivery systems (SEDDS) such as d-a-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Cyclodextrins such as α-, β-, and γ-cyclodextrin, or chemically modified derivatives such as hydroxyalkylcyclodextrins, including 2- and 3-hydroxypropyl-3-cyclodextrins, or other solubilized derivatives may also be advantageously used to enhance delivery. Oil solutions or suspensions may also contain a long-chain alcohol diluent or dispersant, or carboxymethyl cellulose or similar dispersing agents, which are commonly used in the formulation of pharmaceutically acceptable dosage forms such as emulsions and or suspensions.

The compositions are formulated to allow for administration to a subject by any chosen route, including but not limited to oral or parenteral (including topical, subcutaneous, intramuscular and intravenous) administration.

For example, the compositions may be formulated with an appropriate pharmaceutically acceptable carrier (including excipients, diluents, auxiliaries, and combinations thereof) selected with regard to the intended route of administration and standard pharmaceutical practice. For example, the compositions may be administered orally as a powder, liquid, tablet or capsule, or topically as an ointment, cream or lotion. Suitable formulations may contain additional agents as required, including emulsifying, antioxidant, flavouring or colouring agents, and may be adapted for immediate-, delayed-, modified-, sustained-, pulsed- or controlled-release.

In certain embodiments involving the administration of a polypeptide as described herein, administration will typically involve injection or deposition directly into a site of interest, for example, into soft tissue at the site of an injury.

The compositions may be formulated to optimize bioavailability or activity, or to maintain plasma, blood, or tissue concentrations within the therapeutic range, including for extended periods. Controlled delivery preparations may also be used to optimize the bioactive agent concentration at the site of action, for example.

The compositions may be formulated for periodic administration, for example to provide continued exposure.

The compositions may be administered via the parenteral route. Examples of parenteral dosage forms include aqueous solutions, isotonic saline or 5% glucose of the active agent, or other well-known pharmaceutically acceptable excipients. Cyclodextrins, for example, or other solubilising agents well-known to those familiar with the art, can be utilized as pharmaceutical excipients for delivery of the therapeutic agent.

Examples of dosage forms suitable for oral administration include, but are not limited to tablets, capsules, lozenges, or like forms, or any liquid forms such as syrups, aqueous solutions, emulsions and the like, capable of providing a therapeutically effective amount of the composition. Capsules can contain any standard pharmaceutically acceptable materials such as gelatin or cellulose. Tablets can be formulated in accordance with conventional procedures by compressing mixtures of the active ingredients with a solid carrier and a lubricant. Examples of solid carriers include starch and sugar bentonite.

Active ingredients can also be administered in a form of a hard shell tablet or a capsule containing a binder, e.g., lactose or mannitol, a conventional filler, and a tabletting agent. Dosage forms for oral administration can be formulated with an enteric coating to prevent dissolution or disintegration of the dosage form in the stomach to provide for delayed release of the agent and/or to allow release of the agent after the stomach (such as in the upper tract of the intestine).

Examples of dosage forms suitable for transdermal administration include, but are not limited, to transdermal patches, transdermal bandages, and the like.

Examples of dosage forms suitable for topical administration of the compositions include any lotion, stick, spray, ointment, paste, cream, gel, etc., whether applied directly to the skin or via an intermediary such as a pad, patch or the like.

Examples of dosage forms suitable for suppository administration of the compositions include any solid dosage form inserted into a bodily orifice particularly those inserted rectally, vaginally and urethrally.

Examples of dosage of forms suitable for injection of the compositions include delivery via bolus such as single or multiple administrations by intravenous injection, subcutaneous, subdermal, and intramuscular administration or oral administration.

Examples of dosage forms suitable for depot administration of the compositions and include pellets of the peptide or solid forms wherein the peptide is entrapped in a matrix of biodegradable polymers, microemulsions, liposomes or are microencapsulated.

Examples of infusion devices for the compositions include infusion pumps for providing a desired number of doses or steady state administration, and include implantable drug pumps.

Examples of implantable infusion devices for compositions include any solid form in which the bioactive agent is encapsulated within or dispersed throughout a biodegradable polymer or synthetic, polymer such as silicone, silicone rubber, silastic or similar polymer.

Examples of dosage forms suitable for transmucosal delivery of the compositions include depositories solutions for enemas, pessaries, tampons, creams, gels, pastes, foams, nebulised solutions, powders and similar formulations containing in addition to the active ingredients such carriers as are known in the art to be appropriate. Such dosage forms include forms suitable for inhalation or insufflation of the compositions, including compositions comprising solutions and/or suspensions in pharmaceutically acceptable, aqueous, or organic solvents, or mixture thereof and/or powders. Transmucosal administration of the compositions may utilize any mucosal membrane but commonly utilizes the nasal, buccal, vaginal and rectal tissues. Formulations suitable for nasal administration of the compositions may be administered in a liquid form, for example, nasal spray, nasal drops, or by aerosol administration by nebulizer, including aqueous or oily solutions of the polymer particles. Formulations may be prepared as aqueous solutions for example in saline, solutions employing benzyl alcohol or other suitable preservatives, absorption promoters to enhance bio-availability, fluorocarbons, and/or other solubilising or dispersing agents known in the art.

Examples of dosage forms suitable for buccal or sublingual administration of the compositions include lozenges, tablets and the like. Examples of dosage forms suitable for opthalmic administration of the compositions include inserts and/or compositions comprising solutions and/or suspensions in pharmaceutically acceptable, aqueous, or organic solvents.

Examples of formulations of compositions may be found in, for example, Sweetman, S. C. (Ed.). Martindale. The Complete Drug Reference, 33rd Edition, Pharmaceutical Press, Chicago, 2002, 2483 pp.; Aulton, M. E. (Ed.) Pharmaceutics. The Science of Dosage Form Design. Churchill Livingstone, Edinburgh, 2000, 734 pp.; and, Ansel, H. C, Allen, L. V. and Popovich, N. G. Pharmaceutical Dosage Forms and Drug Delivery Systems, 7th Ed., Lippincott 1999, 676 pp. Excipients employed in the manufacture of drug delivery systems are described in various publications known to those skilled in the art including, for example, Kibbe, E. H. Handbook of Pharmaceutical Excipients, 3rd Ed., American Pharmaceutical Association, Washington, 2000, 665 pp. The USP also provides examples of modified-release oral dosage forms, including those formulated as tablets or capsules. See, for example, The United States Pharmacopeia 23/National Formulary 18, The United States Pharmacopeial Convention, Inc., Rockville Md., 1995 (hereinafter "the USP"), which also describes specific tests to determine the drug release capabilities of extended-release and delayed-release tablets and capsules. The USP test for drug release for extended-release and delayed-release articles is based on drug dissolution from the dosage unit against elapsed test time. Descriptions of various test apparatus and procedures may be found in the USP. Further guidance concerning the analysis of extended release dosage forms has been provided by the F.D.A. (See Guidance for Industry. Extended release oral dosage forms: development, evaluation, and application of in vitro/in vivo correlations. Rockville, MD: Center for Drug Evaluation and Research, Food and Drug Administration, 1997).

Where two or more agents are administered or used, the two or more agents may be administered or used simultaneously, sequentially, or separately.

The invention is further described with reference to the following examples. It will be appreciated that the invention as claimed is not intended to be limited in any way by these examples.

EXAMPLES

Example 1: Representative Assay for Bioactive Agents

This example describes the use of ovine forestomach matrix (OFM) in conjunction with macrophages (Mϕ) in a transwell migration bioassay to identify potentially bioactive agents, in this case bioactive agents having chemotactic activity.

Method

Isolation of ovAD-MSC

Ovine adipose derived stomal cells (ovAD-MSC) were isolated from subcutaneous fat tissue from donor animals according to Li et al. (Li, Curley et al. 2018). Adipose tissue was aseptically excised from the shoulder of adult female sheep. Tissue specimens were cut to ~1×1 cm, then rinsed in Dulbeccós Phosphate Buffered Saline (DPBS) (Gibco) (3×, 20 mL) at rt ° C. for 10 mins. Tissues were minced and then digested with 0.1% collagenase/DPBS (10 mL) from *Clostridium histolyticum* (Sigma-Aldrich, St Louis, MI, USA) for 1 h at 37° C., with gentle shaking at 50 rpm. An equal volume of DMEM10 was added and incubated overnight on a 100 mm cell culture plate (Corning, NY, USA). Adherent cells were rinsed (DMEM2, 10 mL) and passaged in DMEM2 for 3 passages. Cells were maintained in DMEM2 (10 mL) with media changed every 3 days and trypsinized using TrypLE™ Express (1.5 mL) (Gibco) once a week.

Differentiation of ovAD-MSC

Cells (ovAD-MSCs, passage 3) were split and seeded onto 24-well plates (Corning) in DMEM2 at a concentration of 100,000 cells/mL (0.5 mL) until monolayers were 80% confluent. Media was changed to osteogenic, chorondrogenic or adipogenic differentiating medias (1 mL) (StemPro™ Osteogenesis Differentiation Kit, Adipogenesis Differentiation Kit, Chondrogenesis Differentiation Kit, Life technologies, Carlsbad, US). Cells were maintained for two weeks in the respective medias, with media changed every 3 days. Differentiated cell monolayers were rinsed in DPBS (1 mL) and then fixed in 10% neutral buffered formalin (1 mL) (Sigma-Aldrich) for 10 mins at rt ° C. Monolayers of adipocytes were stained with Oil Red O (0.5% w/v isopropanol, 1 mL, rt ° C., 10 min) (Sigma-Aldrich) and counter stained with 0.1% haemotoxylin solution (1 mL, rt ° C., 10 min) (Sigma-Aldrich). Osteocytes were stained with 2% Alizarin Red S (1 mL, rt ° C., 10 min) (Sigma-Aldrich). Chondrocytes were stained with Alcian Blue 8XG solution (1 mL, 1% w/v 3% acetic acid, pH 2.5, rt ° C., 10 min) (Sigma-Aldrich). Cultures were rinsed with $ROH_2O$ (3×, 1 mL) then imaged using an Olympus inverted phase contrast and microscope (IX51, Olympus, Tokyo, Japan, data not shown).

Macrophage OFM Co-Culture

OFM was cut to ~4×4 cm samples and pre-conditioned in DMEM (2 mL) at 37° C., for 16 h, in 100 mm culture plates (Corning). RAW 264.7 (ATCC, TIB-71)(Raschke, Baird et al. 1978) macrophages (Mϕ) in DMEM (1 mL at 100,000 cells/mL) were seeded onto OFM (~100,000 cells) and incubated (30 min, 37° C.) to allow cell attachment. Additional DMEM was added to make a final volume of 5 mL per well. Samples were incubated for 24 h at 37° C. As a control, macrophages were seeded onto empty plates at the same concentration. Media was aspirated, collected and phenylmethanesulfonyl fluoride (PMSF) (Sigma-Aldrich) was added at a final concentration of 10 μM. Samples of conditioned media from the respective samples (Mϕ alone, OFM alone, Mϕ+OFM) were sterile filtered (0.22 m) and stored at −20° C. prior to use.

Transwell Migration Assay

Transwell migration assays were conducted according to the method of Boyden et al. (Boyden 1962) using a 24-well transwell system (6.5 mm Transwell®, Corning). Conditioned media samples (OFM, Mϕ and OFM+Mϕ) were diluted 1:1 in DMEM and supplemented with FBS to give a final concentration of 0.5% (DMEM0.5). DMEM0.5 and recombinant human FGF2 (Sigma-Aldrich) (50 ng/mL in DMEM0.5) were used as negative and positive controls, respectively. For each well, 400 μL of each test sample were added to the lower chamber in triplicate. ovAD-MSC (passage 5) were trypsinized using TrypLE™ Express (1.5 mL) (Gibco) counted and resuspended in DMEM0.5 to 100,000 cells/mL. A volume of 100 μL of the cell suspension was plated to the insert (upper chamber). Cultures were incubated for 6 h, then transwell membranes were removed from plates and rinsed with DPBS (500 μL). Non-migrated cells were removed from the inserts using a cotton tip and then inserts were fixed with ice cold methanol (0.5 mL) (Sigma) diluted to 80% v/v in $ROH_2O$ for 10 mins. The fixed inserts were transferred to a new plate containing 0.5 mL of 0.5% (w/v) crystal violet (Sigma-Aldrich) staining solution in 20% methanol/$ROH_2O$ (v/v) for 30 mins. Inserts were rinsed with $ROH_2O$ (3×, 100 mL), then dried. Cells were imaged by inverted microscope (IX51, Olympus, Tokyo, Japan) at 400× magnification, taking five representative images per insert across the entire insert. The number of migrated cells was counted manually using ImageJ (NIH, Bethesda, USA), and multiplied by the area of the membrane (0.33 $cm^2$) to determine the total number of migrated cells per insert. The number of migrated cells was expressed relative to the number of cells that migrated in the media only controls. Results were expressed as Normalized Cell Migration, relative to the media only controls, and represent the average from three independent experiments. Statistical analysis (t-test) was conducted using GraphPad Prism (ver 8.4.1); '*', $p<0.05$; '', $p<0.01$; '*', $p<0.001$; '****', $p<0.0001$.

Results

Figure 3:
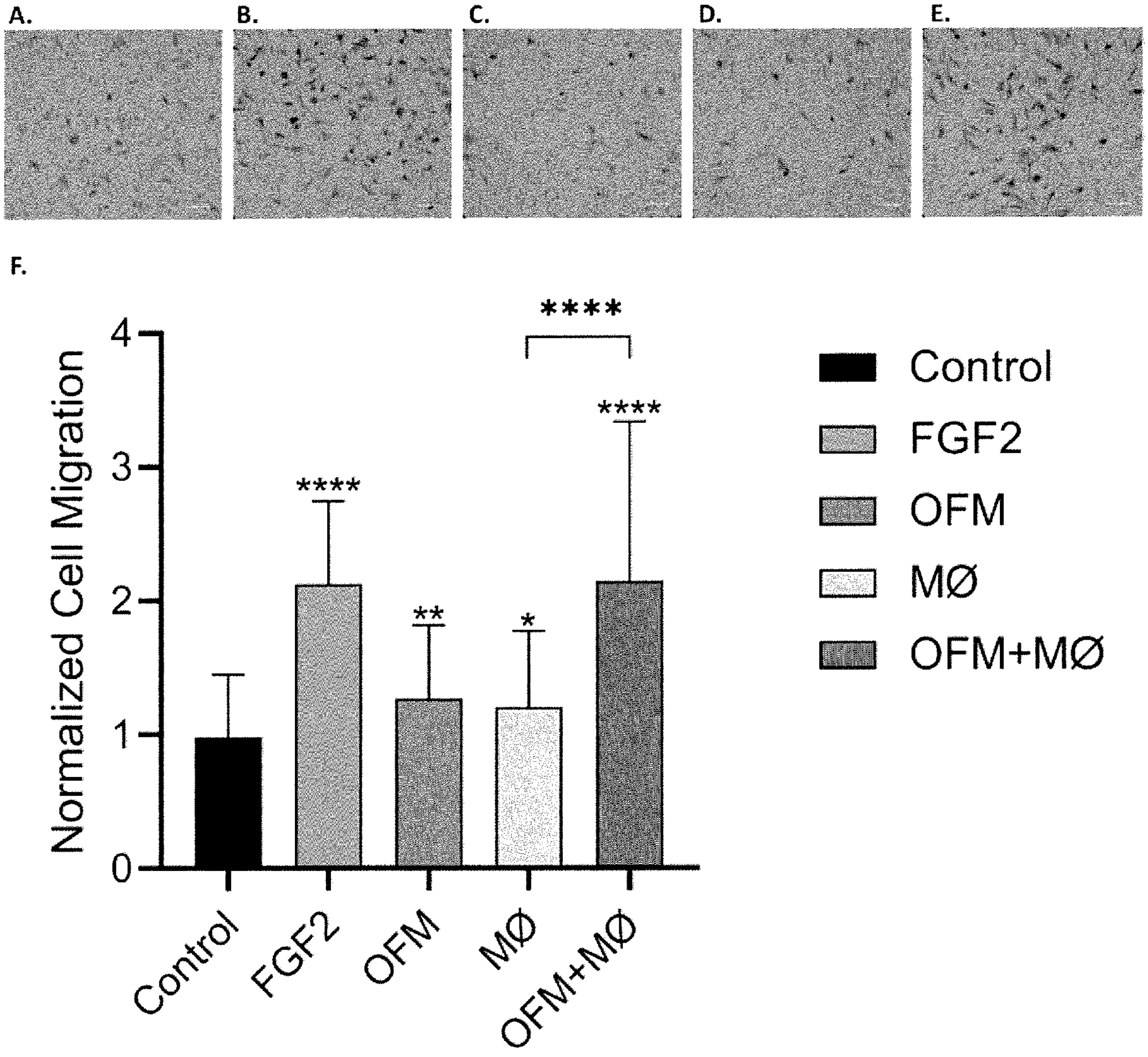
FIG. 3 presents data on the bioactivity of conditioned media in a MSC migration assay as set forth in Example 1 herein, establishing the biological response of MSCs to media produced from a co-culture of macrophages and OFM, compared to OFM alone and to macrophages alone. Conditioned media was generated from culture media containing OFM (OFM), RAW murine macrophage cells (Mϕ), and OFM co-cultured with macrophages (OFM+Mϕ). A transwell migration assay was conducted using ovAD-MSCs, with media alone ('Control') and FGF2 (50 ng/mL), included as the positive and negative controls respectively. Migrated ovAD-MSCs were imaged after 6 h. Representative photomicrographs of test groups are included in panels A through E (A=media control; B=FGF2 (50 ng/mL); C=OFM; D=Mϕ; E=OFM+Mϕ). Cell migration was quantified and results are expressed as the average cell migration normalized to the media control ('Normalized Cell Migration') (F). Error bars represent standard deviation from three independent experiments. Statistical significance was determined via t-test, where; '*'$p \leq 0.05$ ''$p \leq 0.01$ '*'$p \leq 0.001$; '****'$p \leq 0.0001$.

The quantification of mesenchymal stem cell (MSC) chemotaxis in response to OFM alone, macrophages alone, or OFM-macrophage co-culture, is shown in FIG. 3.

As can be readily seen, in this ovAD-MSC migration assay, OFM+Mϕ conditioned media lead to a statistically significant increase in the relative cell migration, compared with the media only control (2.14±1.19 and 0.98±0.47, respectively, FIG. 3). While conditioned media derived from macrophages alone (Mϕ, 1.21±0.57, FIG. 3), and OFM alone (OFM, 1.27±0.55, FIG. 3) did have a significantly increase on the relative cell migration, the combination of both OFM and Mϕ gave the greatest relative cell migration.

Accordingly, culturing macrophages in the presence of OFM was significantly better at recruiting MSC than either OFM, or macrophages, alone.

The inventors believe, without wishing to be bound by any theory, that the observed increase in the potency derived from the OFM+macrophage co-culture is related to the interaction of macrophages and OFM resulting in the production of one or more liberated bioactives from the dECM, wherein the one or more liberated bioactives has improved MSC recruitment compared to the two individual components when separated.

Example 2: Isolation of a Bioactive Polypeptide

This example describes the isolation of a bioactive polypeptide using representative methods as described herein.

Methods

OFM was labelled with a fluorescent tag, fluorescein isothiocyanate (FITC), to enable tracking of the OFM-derived peptides during purification and isolation of the various fractions.

A stock solution of FITC was made up at 10 mg/mL in DMSO and kept as aliquots at −20° C. in a light proof container. A fresh solution of 1 mg/mL FITC was made up fresh in 0.1 M $NaHCO_3$, pH 9.3: this was diluted to give a final working concentration of 10 μg/mL in 10 mL.

OFM (16 mm discs or 4×4 cm squares) were stained by incubation with a 10 μg/mL FITC solution in $NaHCO_3$ in a light proof box on a gentle shaker for 16 hours at 4° C. Unbound FITC was removed by three washes with 10 mL PBS, for 20 minutes with shaking (50 rpm). OFM was conditioned in cell culture media with 1% FBS for 16 hours, and washed a further three times in PBS to remove as much FBS as possible in preparation for cell seeding. Macrophage cells were washed in PBS to remove any FBS and spun down to a density of 1 million cells in 1 mL. Cells in 1 mL were seeded onto 4×4 cm squares of OFM and incubated in petri dishes for 30 minutes to allow for cell attachment, then 10 mL of serum free media was added to each dish. The culture was incubated for 48 hours, before the media was collected and filtered using 0.22 μm syringe driven filters and stored at 4° C.

Gel filtration was employed to isolate any liberated peptides from the filtered media. The buffer for anion exchange was 10 mM tris pH 8.4 or "DEAE buffer". Diethylaminoethyl (DEAE) beads were swollen in 10 mM tris and 1 mL of beads were added to a 15 mL tube using a pipette with the end cut off. Beads were washed three times by filling the tube with 10 mM tris and then centrifuging the beads for ten minutes at 200 rpm, replacing 10 mL of tris buffer with each wash.

A 0.5 mL sample of filtered media solution containing proteins of potential interest was added to 1 mL of DEAE beads. The tube was vortexed for 2 minutes and then left at room temperature for 5 minutes to allow protein binding. The tube was spun for 2 minutes and the supernatant was collected containing unbound proteins. The same volume of DEAE buffer (0.5 mL of 10 mM tris pH 8.4) was added to the DEAE-sample mixture and the tube was vortexed for 1 minute. The tube was centrifuged for 2 minutes and the supernatant was collected containing wash buffer and unbound proteins. A 0.4 mL solution of 10 mM tris with 150 mM NaCl was added to the beads and the tube was vortexed for 2 minutes and then left at room temperature for 5 minutes to allow protein elution. The beads were centrifuged for 2 minutes and the supernatant was collected containing the 150 mM salt eluate. This step was repeated with a solution of 10 mM tris with 400 mM NaCl to collect the 400 mM salt eluate. For each collected fraction, the fluorescence was measured to give a fluorescent index in relation to the initial sample and relative to the volume of the collected fraction. The samples were separated by tricine SDS-PAGE as undiluted samples, and concentrated to tenth the original volume using a speed vacuum.

The fluorescently labelled fractions, containing the OFM-derived peptides of interest, were assayed using an agar-plug chemotaxis assay, as described above in Example 1.

Results

Figure 4:
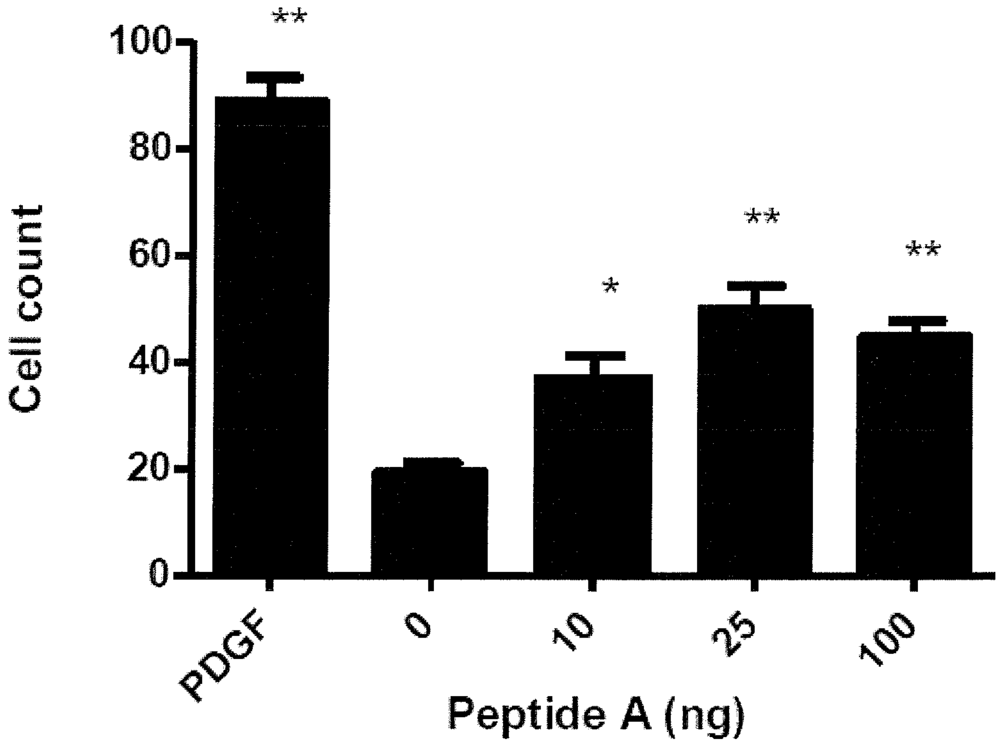
FIG. 4 shows MSC chemotaxis in response to a test sample enriched, via purification, for the protein subsequently identified as the MayDay peptide. Enriched sample of peptide using 10 ng, 25 ng and 100 ng of the total protein. The MayDay enriched samples showed a dose dependent increase in MSC chemotaxis and a significant increase in cell count in calculated by one-way ANOVA compared with media control (0 ng) '*'$p<0.05$, '**'$p \leq 0.01$.

The bioactivity of various amounts of partially purified polypeptide is shown in FIG. 4. As can be seen, 10 ng of partially purified protein is sufficient to elicit a significant increase in MSC chemotaxis compared to a negative control. Still further increased chemotaxis was observed with greater amounts (25 ng, and 100 ng) of the partially purified polypeptide.

Accordingly, the method and assay described in this example is useful in the detection of bioactive polypeptides, and is suitable for the preparation of samples enabling the identification of the bioactive polypeptide(s) in subsequent methods.

Example 3: Identification of a Bioactive Peptide

This example describes the further identification of a bioactive polypeptide that was partially purified in Example 2 above.

Methods

Tris-Glycine SDS-PAGE Separation of Conditioned Media Samples

Samples of conditioned media (30 μL) were diluted 3:1 with 4× Laemmli buffer (100 mM Tris, pH 6.8, 8% w/v SDS, 40% v/v glycerol, 20% w/v β-mercaptoethanol, 0.2% w/v bromophenol blue). Samples were boiled in a water bath at 100° C. for 10 mins. Tris-glycine gels (4% acrylamide stacking gel and a 20% acrylamide resolving gel) were made with a BioRad gel system and run with a glycine running buffer (25 mM Tris, 192 mM glycine, 0.1% w/v SDS, pH 8.3) (Sigma-Aldrich). A total volume of 15 μL of each sample was loaded per well and 8 μL of protein standard ladder (Precision Plus Protein™ Dual Color Standards, BioRad, Hercules, CA, United States). Tris-glycine gels were run for 1 h at 100 V. Fluorescent protein bands were visualized on a Fluoroskan Ascent FL (Thermo Fisher Scientific) before staining with Coomassie brilliant blue (0.1% w/v Coomassie Brilliant Blue R-250, 50% v/v methanol, 10% glacial acetic acid) for 3 h at rt ° C. with gentle shaking. Coomassie stained gel were imaged using a Typhoon FLA 9500 (GE HealthCare, Chicago, IL, USA).

Results

Figure 5:
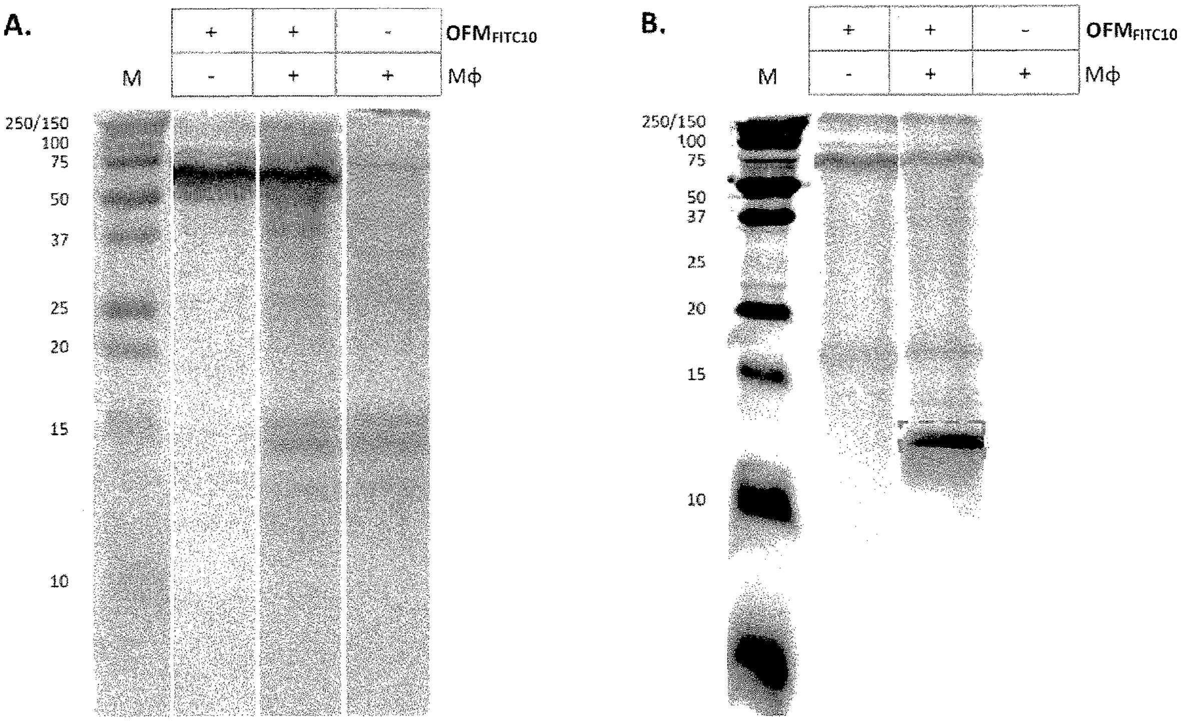
FIG. 5 shows data on conditioned media from cultures of $OFM_{FITC10}$, Mϕ+$OFM_{FITC10}$, and Mϕ alone were separated by Tris-glycine SDS-PAGE electrophoresis. Tris-glycine gels were stained with either Coomassie (A), or imaged via a fluorescence scanner (B). The ~12 kDa protein band of interest highlighted in panel B (blue dashed box).

Samples of conditioned media generated from cultures of $OFM_{FITC10}$, M and $OFM_{FITC10}$+Mϕ were separated on a Tris-glycine gel and imaged via fluorescence of the resultant protein bands (FIG. 5.B). Cultures of macrophages alone did not generate fluorescently labelled proteins (FIG. 5B lane 4), and conditioned media prepared from $OFM_{FITC10}$ alone mainly gave rise to high MW proteins bands (~75-250 kDa, FIG. 5B lane 2). Conditioned media from co-cultures ($OFM_{FITC10}$+Mϕ) gave rise to a distinct fluorescently labelled protein band at ~12 kDa (blue dotted box, FIG. 5B lane 3).

Example 4: Identification of a Bioactive Peptide—'MayDay'

This example describes the identification via mass spectrometry (MS) of a bioactive polypeptide (referred to herein as MayDay) that was partially purified in Examples 2 and 3 above.

Methods

Sample Preparation

OFM (4×4 cm) was labelled with 0 and 10 μg/mL FITC in 0.1 M sodium bicarbonate as described above. The resulting labelled and unlabeled materials (OFM and $OFM_{FITC10}$) were conditioned for 16 h in DMEM (5 mL). OFM and macrophage co-cultures were conducted as described above but the method modified to use ~50,000 cells RAW265.7 macrophages per OFM sample (4×4 cm) in a final volume of 0.5 mL DMEM Cultures were incubated for 24 h and conditioned media from these samples (OFM+Mϕ, $OFM_{FITC10}$+Mϕ and Mϕ alone) were collected. Samples were sterile filtered using 0.22 micron filters and treated with PMSF, as described above. Samples were desalted with PBS (5 mL) and concentrated by ultrafiltration using Amicon Ultra-15 centrifuge filters (Ultracel-PL membrane, 3 kDa, Merk/Millipore, Burlington, Massachusettes, United States) and stored at −20° C. before use.

Protein quantification was carried out using a Bicinchoninic Acid (BCA) kit for protein determination (Sigma-Aldrich) according to the manufacturer's instructions.

In Solution Trypsin Digestion

A sample of Mϕ+OFM was resuspended in PBS to a final protein concentration of 0.1 mg/mL. Samples (20 μg) were reduced with 10 mM 1,4-dithiothreitol (DTT) (Sigma-Aldrich) (20 μL, 60 mins, 60° C.), then alkylated with 20 mM iodoacetamide (Sigma-Aldrich) (20 μL, 30 mins, rt ° C. in the dark). Sample (60 μL) were digested overnight (37° C.) with 0.1 μg trypsin (Sigma-Aldrich). The sample was dried, then reconstituted in loading buffer (0.1 M sodium bicarbonate) prior to ESI MS/MS analysis.

Size Exclusion Chromatography

Lyophilized samples Mϕ+OFM conditioned media, were resuspended in PBS to a final protein concentration of 0.1 mg/mL. Sample (100 μl, ~100 ug) were subjected to size-exclusion chromatography (SEC) (GE Superdex 75 10/300 GL, GE Healthcare, MA, USA) and fractionated into a 96 well plate, using a mobile phase of 50 mM sodium phosphate (pH 7), 150 mM NaCl, and a flow rate of 0.35 mL/min. Elutant was monitored at 214, 220 and 280 nm. Fractions were pooled based on the known retention times and molecular weights of the following standards; aldolase, conalbumin, carbonic anhydrase, RNaseA, and aprotinin. Pooled samples (~1 mL) were reduced with 10 mM DTT at 60° C. for 1 h, then alkylated with 25 mM iodoacetamide (30 mins, rt ° C.). Trypsin (500 ng) was added to each sample, then digested overnight at 37° C. Samples were desalted using a OMIX $C_{18}$ 100 μL tip (Agilent/Varian, A57003100K, Santa Clara, CA, USA), prior to eluting in 100 μL acetonitrile (ACN)/formic acid. The samples were dried, then reconstituted in loading buffer prior to ESI MS/MS analysis.

Tris-Tricine SDS-PAGE and In-Gel Protein Digestion

Samples (Mϕ+OFM, Mϕ+$OFM_{FITC10}$ and Mϕ only) were prepared as described above, then diluted 3:1 with 4× Laemmli buffer and denatured, as described above. A total volume of 15 μL of each sample was loaded per well and 8 μL of protein standard ladder (Precision Plus Protein™ Dual Color Standards, BioRad). Tris-Tricine gels (4% acrylamide stacking gel and a 16% acrylamide resolving gel) were run using a cathode buffer (100 mM Tris, 100 mM tricine, 0.1% w/v SDS, pH 8.25) and an anode buffer (100 mM Tris, pH 8.9). Gels were run for 2 h at 60 V on ice (~4° C.). Tris-Tricine gels were fluorescently visualized on a Fluoroskan Ascent FL (Thermo Fisher Scientific) before staining with Coomassie brilliant blue (0.1% Coomassie Brilliant Blue R-250, 50% v/v methanol and 10% glacial acetic acid) for 3 h at rt ° C. with gentle shaking. Coomassie stained gel were imaged using a Typhoon FLA 9500 scanner (GE Healthcare, Chicago, IL, USA).

The area of interest, corresponding to the band with MW 12 kDa was excised from the gel from lanes containing both Mϕ+OFM, Mϕ+$OFM_{FITC10}$. Sample was reduced with DTT (10 mM, 20 μL) for 1 h at 60° C., then alkylated with iodoacetamide (20 mM, 20 μL) for 30 mins in dark at room temperature. Proteins were digested with 100 ng of trypsin overnight at rt ° C. Sample was concentrated to 30 μL, prior to ESI MS/MS.

ESI MS/MS Analysis

Injections were made to an Eksigent Ultra nanoLC system (Eksigent, Livermore, CA USA), coupled to a Triple TOF 5600 (AB Sciex, Redwood City, CA, USA). Digested sample (10, 20 or 40 μL) was injected onto a peptide trap (peptide Captrap, Michrom Bioresources, Auburn, CA, USA) and desalted with 0.1% aqueous formic acid/2% acetonitrile (ACN), at 10 μL/min for 5 mins. The peptide trap was then switched into line to an analytical column (Halo C18, 160 Å, 2.7 μm, 75 μm×10 cm, Advances Materials Inc., Wilmington, DE, USA). Peptides from trypsin digested samples and in-gel digested samples, were eluted from the column using a solvent gradient; 95% (aqueous 0.1% formic acid)/5% (99.9% ACN/0.1% formic acid) to 60% (aqueous 0.1% formic acid)/40% (99.9% ACN/0.1% formic acid), at a flow rate of 550 nL/min over a 42 min period. Peptides from SEC were eluted from the column using a solvent gradient; $H_2O$:ACN (95:5; +0.1% formic acid) to $H_2O$:ACN (5:95; +0.1% formic acid) with constant flow (500 nL/min) over an 80 min period.

The eluent was subject to positive ion nanoflow electrospray analysis in an information dependent acquisition (IDA) mode. In IDA mode a TOFMS survey scan was acquired (m/z 350-1500, 0.25 second), with the ten most intense multiply charged ions (counts >150) in the survey scan sequentially subjected to MS/MS analysis. MS/MS spectra were accumulated for 200 milliseconds in the mass range m/z 100-1500 with the total cycle time 2.3 seconds. The raw data files (.wiff) were converted to mascot generic files (.mgf) using AB SCIEX CommandDriver software (AB SCIEX, Redwood City, CA, USA). Data files were submitted to Mascot (Matrix Science, UK) and searched against Swissprot database (*Ovis aries* [sp_sheep_140625].

Results

A large volume of conditioned media prepared from $OFM_{FITC10}$+Mϕ and OFM+Mϕ was prepared and MS analysis proceeded on samples prepared via three different methods; 1. an in solution tryspin digest of the conditioned media; 2. size-exclusion chromatography purification; 3. 1-D Tris-Tricine gel separation and in-gel trypsin digest. The ~12 kDa protein of interest was clearly resolved via Tris-Tricine gel (data not shown). In each approach samples of both $OFM_{FITC10}$+Mϕ and OFM+Mϕ were analyzed, using the FITC sample as a means to track the protein(s) of interest via fluorescence. ESI MS/MS analysis was conducted on OFM+Mϕ samples only, in order to avoid any complications due to the FITC label. The MASCOT database was used to identify all identified protein fragments from the three sample preparation methods.

The ECM protein decorin (DCN) was consistently identified from the MASCOT search results. The database search identified several unique peptides shown below as a match (emPAI: 0.08) for the ovine protein Decorin (Uniprot: Q9TTE2, also known as Bone proteoglycan II, PG-S2, PG40, with a mass of 39947 Da).

The peptides identified via the three different methods are shown in FIG. 6A. The in-solution trypsin digested sample yielded the most protein hits that spanned much of the DCN sequence ('blue', FIG. 6A). This most likely results from the relative impurity of the trypsin digested sample. The sample prepared via SEC gave one sequence that aligned a N-terminal sequence of DCN ('yellow', FIG. 6A), and the sample prepared from a Tris-Tricine gel gave a further sequence also aligned to the N-terminal region of DCN ('green', FIG. 6A). The sequence of these latter two unique peptides is presented below:

1. KISPGAFAPLVKL

2. RVVQCSDLGLEKV

Table 1 below presents the amino acid sequence of the full length Decorin protein [Sequence ID No: 1], with the amino acid sequences corresponding to these two unique peptides shown in underline. FIG. 6A shows the location of other unique peptides within the Decorin sequence within the N-terminal portion of Decorin, while the location of the MMP12 proteolytic cleavage sites are shown in FIG. 6B). The amino acid sequence of Decorin corresponding to the recombinant MayDay31-170 polypeptide [Sequence ID No:2], and that corresponding to two N-terminal fragments of Decorin each terminating at an MMP12 cleavage site, MayDay31-177 [Sequence ID No:3], and MayDay31-188 [Sequence ID No:4], respectively, are depicted in Table 1. Again, the location of the amino acid sequences corresponding to these two unique peptides depicted above is shown in underline.

TABLE 1

Decorin and MayDay peptide

| Sequence | SEQ ID No. |
|---|---|
| MKATIIFFLV AQVSWAGPFQ QKGLFDFMLE DEASGIGPEE<br>RFHEVPELEP MGPVCPFRCQ CHLRVVQCSD LGLEKVPKDL<br>PPDTALLDLQ NNKITEIKDG DFKNLKNLHT LILINNKISK<br>ISPGAFAPLV KLERLYLSKN QLKELPEKMP KTLQELRVHE<br>NEITKVRKSV FNGLNQMIVV ELGTNPLKSS GIENGAFQGM<br>KKLSYIRIAD TNITTIPQGL PPSLTELHLD GNKITKVDAA<br>SLKGLNNLAK LGLSFNSISA VDNGSLANTP HLRELHLNNN<br>KLVKVPGGLA DHKYIQVVYL HNNNISAIGS NDFCPPGYNT<br>KKASYSGVSL FSNPVQYWEI QPSTFRCVYV RAAVQLGNYK | 1 |
| DEASGIGPEE RFHEVPELEP MGPVCPFRCQ CHLRVVQCSD<br>LGLEKVPKDL PPDTALLDLQ NNKITEIKDG DFKNLKNLHT<br>LILINNKISK ISPGAFAPLV KLERLYLSKN QLKELPEKMP<br>KTLQELRVHE NEITKVRKSV | 2 |
| DEASGIGPEE RFHEVPELEP MGPVCPFRCQ CHLRVVQCSD<br>LGLEKVPKDL PPDTALLDLQ NNKITEIKDG DFKNLKNLHT<br>LILINNKISK ISPGAFAPLV KLERLYLSKN QLKELPEKMP<br>KTLQELRVHE NEITKVRKSV FNGLNQM | 3 |
| DEASGIGPEE RFHEVPELEP MGPVCPFRCQ CHLRVVQCSD<br>LGLEKVPKDL PPDTALLDLQ NNKITEIKDG DFKNLKNLHT<br>LILINNKISK ISPGAFAPLV KLERLYLSKN QLKELPEKMPK<br>TLQELRVHE NEITKVRKSV FNGLNQMIVV ELGTNPLK | 4 |

A computational analysis was conducted using the MERPOS database to predict the proteolytic cleavage sites of ovine DCN, based on sequence homology to known human DCN cleavage sites. As shown in FIG. 6B, DCN contains a number of predicted protease sites including MMP-2, -3, -7, -12 and -13, as well as ADAMTs5. Notably, two MMP-12 sites were predicted to occur between residues 177-178 and 188-189.

Example 5: Production and Assessment of Bioactive MayDay Peptide Via MMP12 Digestion of Decorin This example describes the production of the MayDay polypeptide identified in Example 4, and an assessment of its bioactivity using the MMP12 to cleave the parent protein.

Methods

Stock solutions of MMP-12 catalytic domain (Sino Biologicals, Beijing China), and DCN (Sino Biologicals) were prepared 0.25 mg/mL in $ROH_2O$, and stored at −20° C. prior to use. Samples of DCN (10 μL) were digested with 0, 0.1, 5, or 10 μL the MMP-12 solution, to give protein:enzyme ratios of 1:1, 2:1, 100:1. Final volumes of the samples were made up to 40 μL with MMP-12 buffer (50 mM Tris, NaCl 100 mM, 0.05% w/v Brij35, pH 8.0). The samples were incubated at 37° C. for 16 h, with gentle shaking.

Digested Samples (30 μL) were diluted 3:1 with 4× Laemmli buffer and denatured, as described above. A total volume of 30 μL was loaded onto precast Bis-Tris gels (4-12% Bolt NuPAGE, Invitrogen, Carlsbad, CA, USA). Bis-Tris gels were run with a protein standard solution (5 μL) (SeeBlue protein standard, Invitrogen). Gels were run using an Invitrogen Mini Gel system (Invitrogen™) in a BOLT running buffer (Bolt™ MES SDS Running Buffer, Invitrogen™) for 90 mins at 100 V. Gels were rinsed (3×, $ROH_2O$, 10 mL) and then stained with Coomassie as described above.

Figure 7A:
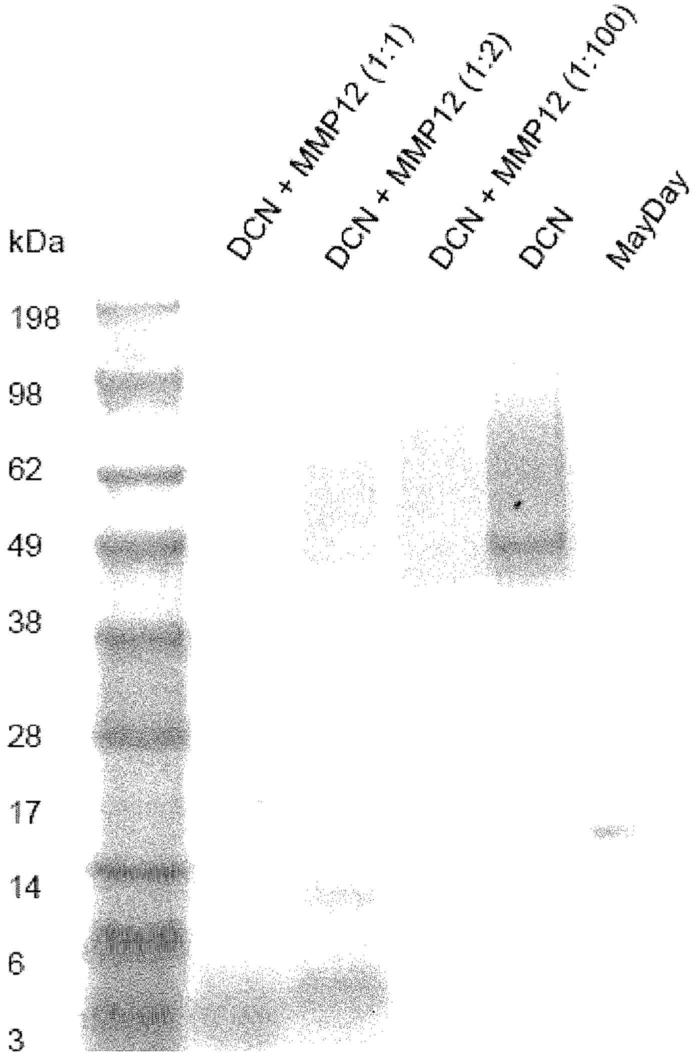
FIG. 7 shows the cleavage in vitro of Decorin protein present in OFM by macrophage derived MMP12 (see FIG. 6A) giving rise to the MayDay peptide (FIG. 7A, lane 6). The MayDay peptide exhibits greater chemotactic activity than full-length Decorin, as shown in FIG. 7B. Recombinant human DCN was digested with MMP-12 prior to a transwell migration assay was conducted using ovAD-MSCs. Media alone ('Control') and FGF2 (50 ng/mL), included as the positive and negative controls, respectively. Migrated ovAD-MSCs were imaged after 6 h. Representative photomicrographs of test groups are included in panels A through E (A=media control; B=FGF2 (50 ng/mL); C=MMP12; D=DCN; E=MMP12+DCN). Cell migration was quantified and results are expressed as the average cell migration normalized to the media control ('Normalized Cell Migration') (F). Error bars represent standard deviation from three independent experiments. Statistical significance was determined via t-test, where; ''$p \leq 0.01$ '*'$p \leq 0.001$; '****'$p \leq 0.0001$.

Decorin and MMP12-digested Decorin were analysed on an SDS page gel to demonstrate fragmentation of the protein, as shown in FIG. 7A.

Following this, samples were added to a transwell assay using Decorin+MMP12 to determine the bioactivity of these samples, with a control of DCN alone (250 ng), and MMP12 alone (25 ng).

For transwell migration assays, samples were prepared as follows: DCN (20 μL at 0.25 mg/mL) and MMP-12 (10 μL at 0.25 mg/mL) were made up in to 40 μL with digestion buffer giving a protein:enzyme ratio of 2:1, as described above. As controls, DCN alone (20 μL at 0.25 mg/mL) and MMP-12 alone (10 μL at 0.25 mg/mL) were made up to 40 μL with digestion buffer and a sample of digestion buffer alone ('control') were incubated for the same length of time. The samples were incubated overnight at 37° C. for 16 h. After incubation each solution was combined with 0.5 mL of DMEM0.5 to quench enzymatic digestion. Transwell migration assay using ovAD-MSC cells was conducted as described above. Images of membranes were acquired and migrated cells were counted using ImageJ. Results were expressed as Normalized Cell Migration, relative to the media only samples, and represent the average from three independent experiments. Statistical analysis (t-test) was conducted using GraphPad Prism (ver 8.4.1); '*', $p<0.05$; '', $p<0.01$; '*', $p<0.001$; '****', $p<0.0001$.

Results

Figure 7B:
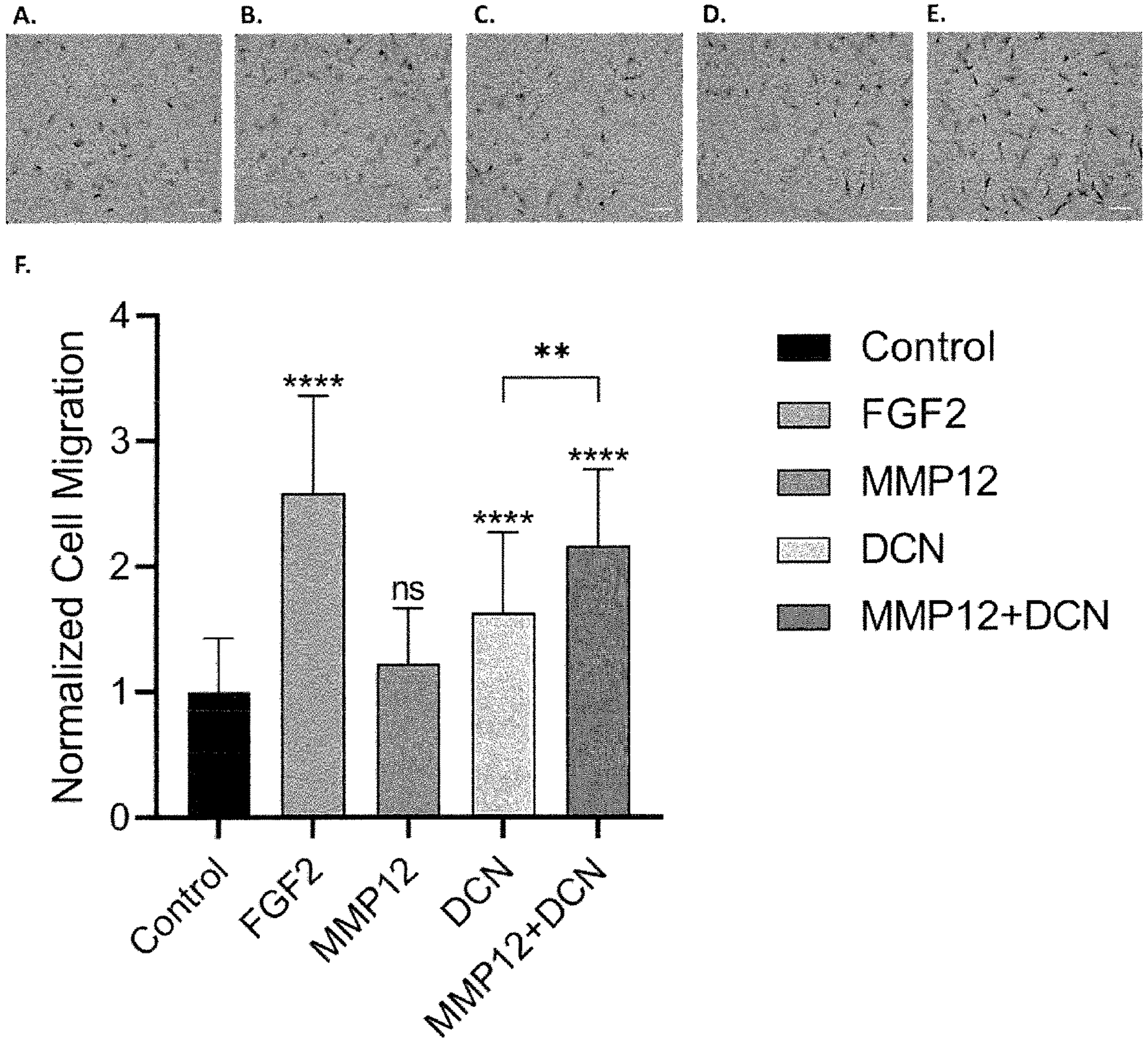

The number of migrated cells present on the lower chamber of the transwell membranes is shown in FIG. 7B. As can clearly be seen, a greater number of cells migrate to the lower chamber in the presence of Decorin when it has been digested with MMP12. In comparison, fewer cells were observed with media-only negative control samples and with undigested Decorin protein.

This example demonstrates the ability of enzymatically produced MayDay protein to elicit cell recruitment comparable to that observed with MayDay polypeptide derived from OFM+macrophage cultures. Accordingly, this example establishes that the biological activity of a bioactive polypeptide identified in an analytical method as described herein can be recapitulated by a synthetically produced polypeptide.

Example 6: Production and Assessment of Recombinant Bioactive MayDay Peptide This example describes the recombinant production of the MayDay polypeptide identified herein, and an assessment of its bioactivity.

Methods

Recombinant HIS tagged MayDay(31-170) (rec-HIS-ovMayDay(31-170)) was expressed and purified by Biomatik (Ontario, Canada), according to established procedures. Briefly, the ovine DCN sequence 31-170 with a 6×His-tag fused to its N-terminus was cloned into a pET30a cloning vector. The expression plasmid was transformed into *E. coli* BL21 cells and cells grown at 37° C. in Luria Broth (LB) media supplemented with 50 μg/mL Kanamycin (Sigma-Aldrich) until OD600 nm 0.6 was reached, then Isopropyl β-d-1-thiogalactopyranoside (IPTG) (0.2 mM) (Sigma-Aldrich) was added into the media, and the cells was further incubated for 16 h at 15° C. The cell suspension was sonicated with lysis buffer (50 mM Tris, pH 8.5, 300 mM NaCl, 20 mM imidazole) (Sigma-Aldrich). The supernatant was loaded onto a Ni-IDA affinity column pre-equilibrated with lysis buffer, centrifuged and supernatant collected. Fractions were analyzed by SDS-PAGE. Fractions were pooled and dialyzed against the final buffer (50 mM Tris, pH 8.5, 150 mM NaCl).

Recombinant His-tagged MayDay (31-171) (rec-HIS-ovMayDay(31-170)) was tested in a transwell migration assay using ovAD-MSC, as described above. rec-HIS-ovMayDay(31-170) was a prepared in PBS (0.1 mg/mL), then diluted to a final concentration of 0.05, 0.50 and 5.00 ng/mL in DMEM0.5. Human recombinant SDF-1 (Sigma) was prepared in PBS (0.1 mg/mL) and diluted to a final concentration of 50 ng/mL in DMEM0.5. Images of membranes were acquired and migrated cells were counted using ImageJ. Results were expressed as Normalized Cell Migration, relative to the media only samples, and represent the average from three independent experiments. Statistical analysis (t-test) was conducted using GraphPad Prism (ver 8.4.1); '*', $p<0.05$; '', $p<0.01$; '*', $p<0.001$; '****', $p<0.0001$.

Results

Figure 8:
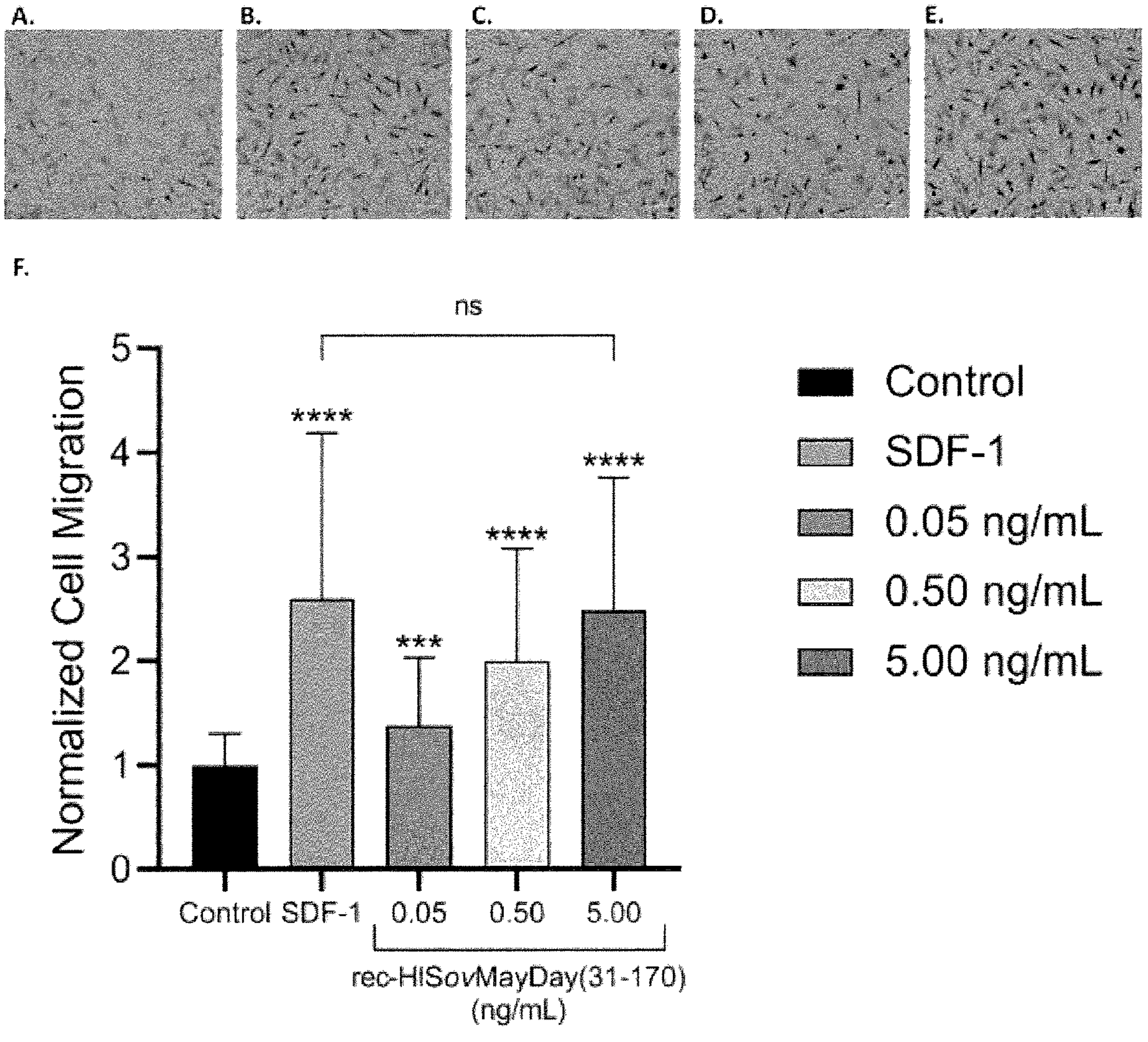
FIG. 8 shows data depicting the bioactivity of recombinant MayDay peptide in MSC cell recruitment compared to the growth factor SDF1 (stromal derived growth factor), as described in Example 6. Recombinant HIS-tagged MayDay (31-170) [rec-HISovMayDay(31-170)] was assayed at three concentrations using a transwell assay using ovAD-MSC. Media alone ('Control') and SDF-1 (50 ng/mL), included as the positive and negative controls, respectively. Migrated ovAD-MSCs were imaged after 6 h. Representative photomicrographs of test groups are included in panels A through E (A=media control; B=SDF-1 (50 ng/mL); C=0.05 ng/mL; D=0.50 ng/mL; E=5.00 ng/mL). Cell migration was quantified and results are expressed as the average cell migration normalized to the media control ('Normalized Cell Migration') (F). Error bars represent standard deviation from three independent experiments. Statistical significance was determined via t-test, where; '*'$p \leq 0.001$; '**'$p \leq 0.0001$.

The number of migrated cells present on the lower chamber of the transwell membranes is shown in FIG. 8. As can clearly be seen, the presence of as little as 5 ng/mL recombinant MayDay polypeptide elicited substantial cell migration, comparable to that observed with 50 ng/mL SDF1. In comparison, very few cells were observed with media-only negative control samples.

This example demonstrates the ability of recombinantly produced MayDay protein to elicit cell recruitment comparable to that observed with MayDay polypeptide derived from OFM+macrophage cultures. Accordingly, this example establishes that the biological activity of a bioactive polypeptide identified in an analytical method as described herein can be recapitulated by a recombinantly expressed polypeptide.

Example 7: In Vivo Assessment of Recombinant MayDay Peptide Bioactivity

This example describes the assessment of a recombinant MayDay polypeptide in an in vivo model of MSC recruitment.

Methods

Recombinant MayDay(31-170) Expression

Tag free protein (rec-ovMayDay(31-170)) was expressed as described above using a pSUMO vector to in BL21 *E. coli* cells. After expansion and expression, the supernatant was loaded onto a Q Sepharose™ fast flow pre-equilibrated with lysis buffer, centrifuged and the supernatant fraction was analyzed by SDS-PAGE. Purity (>85%) was confirmed by SDS PAGE. Lyophilized proteins were stored at −20° C.

Fluorescent Labelling of muBM-MSC muBM-MSC were labeled immediately prior to injection into Balb/c mice using the Cellvue NIR815 fluorescent cell labeling kit (Licor, Lincoln, US). A plate of muBM-MSC at 80% confluency where resuspended in DMEM (5 mL), centrifuged and resuspended in Diluent C (Licor, Lincoln, US) to give a final concentration of $2\times10^7$ cells/mL. Cells were labeled with a near infrared dye (NIR815), as per manufacturer's instructions. Briefly, CellVue dye stock solution (2 μL, $4\times10^{-6}$ M) was added to Diluent C (1 mL). The dye was then added to muBM-MSC in Diluent C (1 mL) and incubated at 37° C. for 5 mins. The reaction was quenched with FBS (2 mL). Cells were pelleted by centrifugation at 400 rpm for 10 mins, then rinsed with PBS (3×, 10 mL). After final wash cells were resuspended in complete medium (5 mL) and held at 37° C. prior to use.

In Vivo MSC Chemotaxis

Test articles, recombinant MayDay (rec-ovMayDay31-170), and human recombinant SDF-1 (Sigma) were prepared in 0.9% sterile saline (Braun, Melsungen, Germany). Five treatment groups were used; rec-ov MayDay(31-170) [1 μg/animal, (~0.05 μg/kg); 10 g/animal (~0.5 mg/kg) and 25 μg/animal (~1.25 mg/kg)]; SDF-1 10 μg/animal, (~0.5 mg/kg) and 0.9% sterile saline. Balb/c mice were anesthetized using isoflurane and placed in a ventral recumbency with anesthetic gas administered via nose cone. The injection sites (hind limb and tail) were prepared with chlorhexidine wipes. Test articles were administered to the Balb/c mice (n=3 per test article) via a 30 μL intramuscular injection to the right hind-limb muscle ('treated').

After 5-10 mins NIR815 labelled muBM-MSC (~$5\times10^6$ cells) were injected (5 mL/kg) into the tail vein of each animal. Animals were imaged using an optical imaging system (Pearl Trilogy, Licor, Lincoln, US) at pre-determined timepoints; 0, 3, 6, 12 and 24 h after administration of the labelled muBM-MSC. After 24 h animals were euthanized by cervical dislocation. Hindlimb muscle tissue from the 'treated' sites were dissected, as well as a matched 'normal' tissue from the left hind limb of each animal. Additionally, major organs (brain, spleen, liver, gut, kidney and lung) were harvested from all animals.

Explanted 'treated' and 'normal' muscle tissue was imaged using 800 nm channel (ex: 786 nm, em: 814 nm) using the Pearl Trilogy imaging system and a fluorescence signal (pixels) determined for each, using Image studio software (ver 5.2, Licor). For each sample a background fluorescence signal (pixels) was also measured, based on an equivalent area ($cm^2$) of the tissue sample. Sample fluorescence was determined based on the signal of the test sample ('treated' and 'normal'), minus the corresponding background fluorescence.

The multipotency of the isolated muBM-MSC was verified by tri-lineage differentiation assay (osteogenesis, adipogenesis, and chondrogenesis) (data not shown)

Results

Animals that were injected with the recombinant MayDay peptide demonstrated donor cell recruitment to the injection site, as readily seen in FIG. 9. No significant cell recruitment to the injection site was observed with vehicle-only control.

Figure 9A:
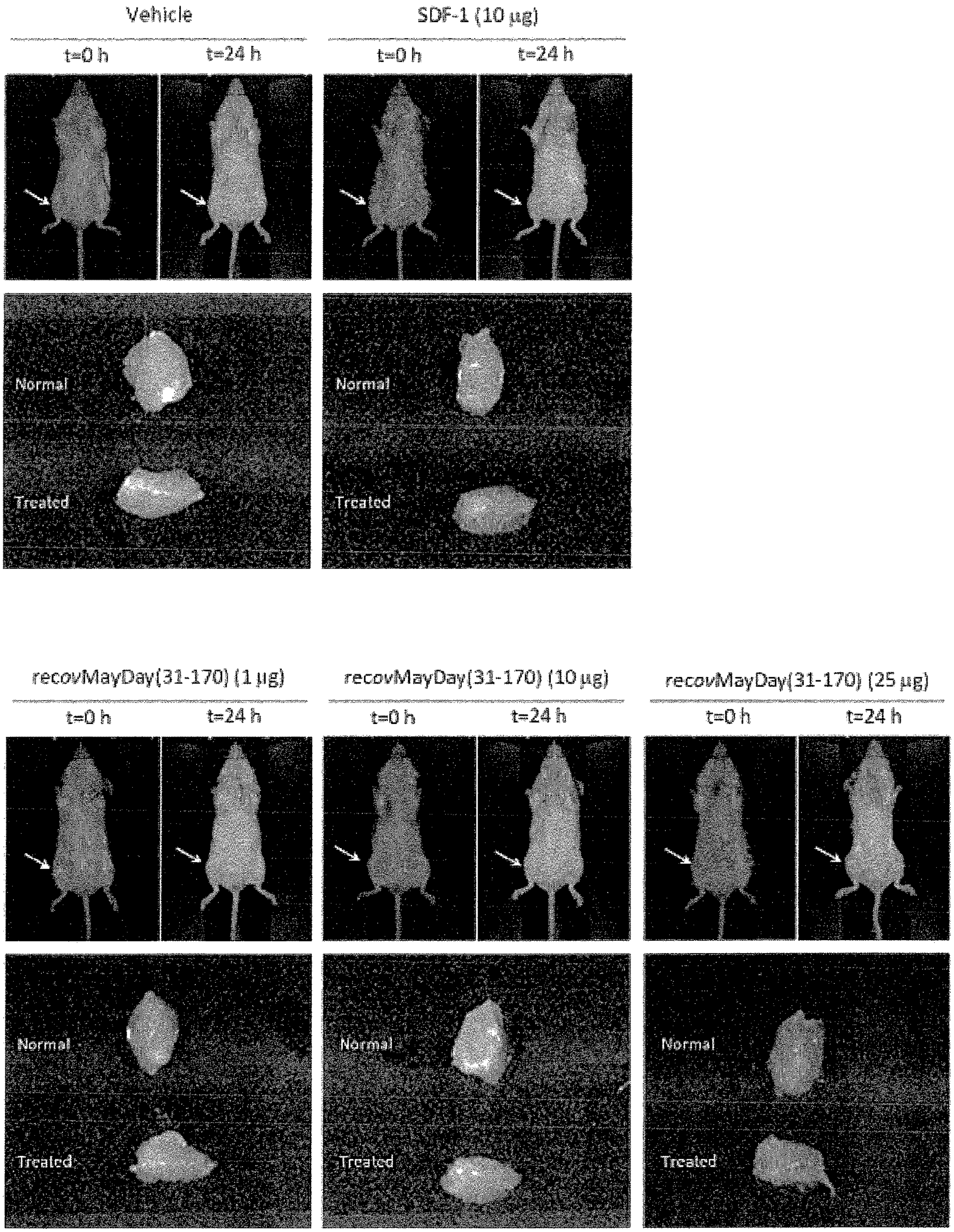
FIG. 9A shows representative images of animals (top panels) from each of the treatment groups at t=0 and t=24 h post injection of labelled muBM-MSC. Arrows indicate the injection site for each of the treatment groups. Representative images of excised 'normal' and 'treated' muscle tissue are also presented (bottom panels).

At all concentrations of rec-ovMayDay(31-170) tested there was a significant increase in the localization of muBM-MSC to the injection site ('normal' vs 'treated', FIG. 9A), suggesting recruitment of muBM-MSC to the site of rec-ovMayDay(31-170) administration. Sites receiving higher concentrations of 10 and 25 μg rec-ovMayDay(31-170) ('treated', FIG. 9A) showed significantly more local muBM-MSC recruitment, relative to sites receiving the vehicle-only control. Substantially increased fluorescence resulting from cell recruitment was observed in excised muscle tissue from animals injected with rec-ovMayDay(31-170) compared to normal controls, and the observed fluorescence in excised tissue increased with increasing rec-ovMayDay(31-170) concentration (FIG. 9A, bottom panels).

Figure 9B:
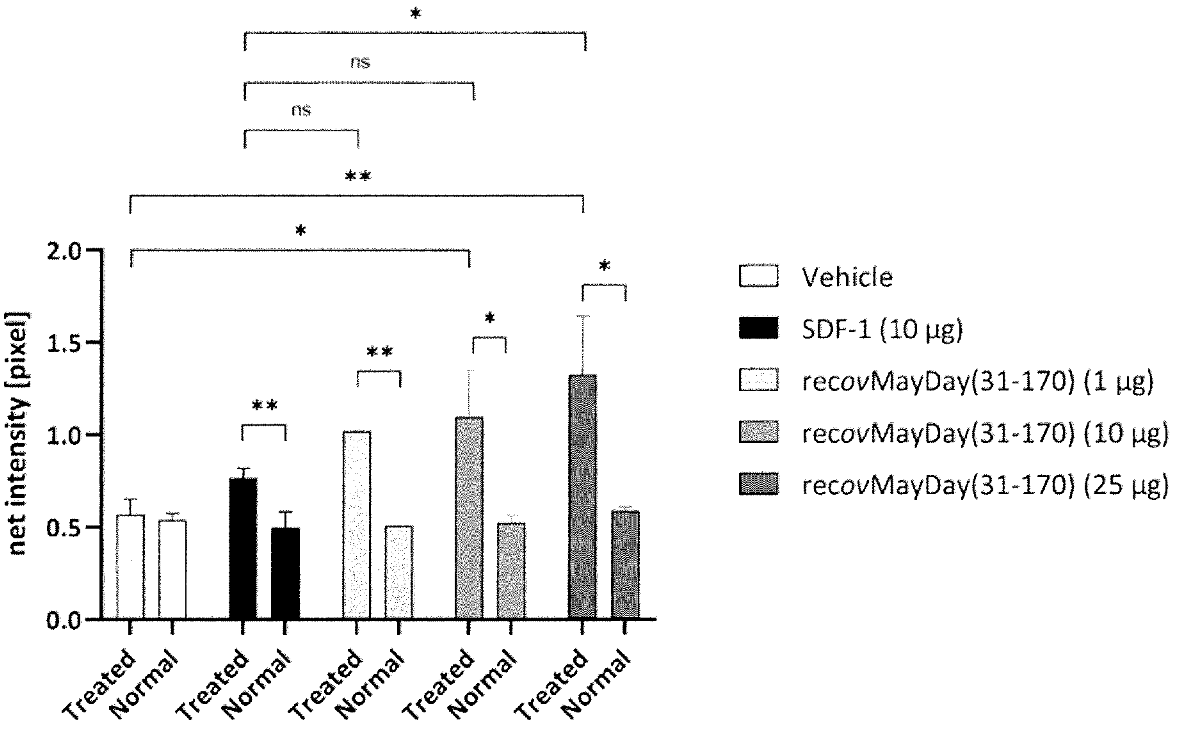
FIG. 9B shows the quantification of fluorescence intensity (pixels) of excised 'normal' and 'treated' muscle tissue for each of the treatment groups. Error bars represent standard error form triplicate animals. Statistical significance was determined via t-test, where; '*'$p \leq 0.05$, '**'$p \leq 0.01$.

Signal intensity at the injection site was quantitated and the results presented in FIG. 9B, clearly showing the increased cell recruitment on administration of recombinant MayDay peptide, and to a lesser extent, with SDF1 administration. The highest 25 μg dose of rec-ovMayDay(31-170) gave significantly more muBM-MSC localization than the control, SDF-1 at 10 μg.

These examples clearly demonstrate that bioactive agents can be prepared, isolated, identified and produced (including by recombinant methods) using the methods described herein, and that the bioactivity of such agents can be assessed and utilised to provide bioactive agents having research, diagnostic, and therapeutic value.

PUBLICATIONS

Bellon, G., L. Martiny and A. Robinet (2004). "Matrix metalloproteinases and matrikines in angiogenesis." *Crit Rev Oncol Hematol* 49(3): 203-220.

Boyden, S. (1962). "The chemotactic effect of mixtures of antibody and antigen on polymorphonuclear leucocytes." *J Exp Med* 115: 453-466.

Larjava, H., T. Salo, K. Haapasalmi, R. H. Kramer and J. Heino (1993). "Expression of integrins and basement membrane components by wound keratinocytes." *J Clin Invest* 92(3): 1425-1435.

Li, J., J. L. Curley, Z. E. Floyd, X. Wu, Y. D. C. Halvorsen and J. M. Gimble (2018). "Isolation of human adipose-derived stem cells from lipoaspirates." *Methods Mol Biol* 1773: 155-165.

Maquart, F. X., S. Pasco, L. Ramont, W. Hornebeck and J. C. Monboisse (2004). "An introduction to matrikines: extracellular matrix-derived peptides which regulate cell activity. Implication in tumor invasion." *Crit Rev Oncol Hematol* 49(3): 199-202.

Raschke, W. C., S. Baird, P. Ralph and I. Nakoinz (1978). "Functional macrophage cell lines transformed by Abelson leukemia virus." *Cell* 15(1): 261-267.

Ricard-Blum, S. and R. Salza (2014). "Matricryptins and matrikines: biologically active fragments of the extracellular matrix." *Experimental Dermatology* 23(7): 457-463.

Tran, K. T., P. Lamb and J. S. Deng (2005). "Matrikines and matricryptins: Implications for cutaneous cancers and skin repair." *J Dermatol Sci* 40(1): 11-20.

As used in this specification, the words "comprise", "comprises", "comprising", and similar words, are not to be interpreted in an exclusive or exhaustive sense. In other words, they are intended to mean "including, but not limited to". When interpreting each statement in this specification that includes the term "comprise", "comprises", or "comprising", features other than that or those prefaced by the term may also be present.

The entire disclosures of all applications, patents and publications cited above and below, if any, are herein incorporated by reference.

Where in the foregoing description reference has been made to integers or components having known equivalents thereof, those integers are herein incorporated as if individually set forth.

It should be noted that various changes and modifications to the presently preferred embodiments described herein will be apparent to those skilled in the art. Such changes and modifications may be made without departing from the spirit and scope of the invention and without diminishing its attendant advantages. It is therefore intended that such changes and modifications be included within the present invention.

The invention may also be said broadly to consist in the parts, elements and features referred to or indicated in the specification of the application, individually or collectively, in any or all combinations of two or more of said parts, elements or features.

Aspects of the invention have been described by way of example only, and it should be appreciated that variations, modifications and additions may be made without departing from the scope of the invention, for example when present the invention as defined in the indicative claims. Furthermore, where known equivalents exist to specific features, such equivalents are incorporated as if specifically referred in this specification.

SEQUENCE LISTING

<110> Aroa Biosurgery Limited

May, Barnaby

Dempsey, Sandi

Day, Darren

<120> BIOACTIVE AGENTS AND METHODS RELATED THERETO

<130> MES1013PC

<150> U.S. Pat. No. 62/857,900

<151> 2019-06-06

<150> U.S. Pat. No.63/014,530

<151> 2020 Apr. 23

<160> 4

<170> PatentIn version 3.5

<210> 1

<211> 360

<212> PRT

<213> Ovis aries

<400> 1

```
Met Lys Ala Thr Ile Ile Phe Phe Leu
1               5

Val Ala Gln Val Ser Trp Ala Gly Pro
10              15

Phe Gln Gln Lys Gly Leu Phe Asp Phe
    20                  25

Met Leu Glu Asp Glu Ala Ser Gly Ile
        30                  35

Gly Pro Glu Glu Arg Phe His Glu Val
            40                  45

Pro Glu Leu Glu Pro Met Gly Pro Val
                50

Cys Pro Phe Arg Cys Gln Cys His Leu
55              60

Arg Val Val Gln Cys Ser Asp Leu Gly
    65                  70
```

```
Leu Glu Lys Val Pro Lys Asp Leu Pro
        75                  80

Pro Asp Thr Ala Leu Leu Asp Leu Gln
            85                  90

Asn Asn Lys Ile Thr Glu Ile Lys Asp
                95

Gly Asp Phe Lys Asn Leu Lys Asn Leu
100                 105

His Thr Leu Ile Leu Ile Asn Asn Lys
    110                 115

Ile Ser Lys Ile Ser Pro Gly Ala Phe
        120                 125

Ala Pro Leu Val Lys Leu Glu Arg Leu
            130                 135

Tyr Leu Ser Lys Asn Gln Leu Lys Glu
                140

Leu Pro Glu Lys Met Pro Lys Thr Leu
145                 150

Gln Glu Leu Arg Val His Glu Asn Glu
    155                 160

Ile Thr Lys Val Arg Lys Ser Val Phe
        165                 170

Asn Gly Leu Asn Gln Met Ile Val Val
            175                 180

Glu Leu Gly Thr Asn Pro Leu Lys Ser
                185

Ser Gly Ile Glu Asn Gly Ala Phe Gln
190                 195

Gly Met Lys Lys Leu Ser Tyr Ile Arg
    200                 205

Ile Ala Asp Thr Asn Ile Thr Thr Ile
        210                 215

Pro Gln Gly Leu Pro Pro Ser Leu Thr
            220                 225

Glu Leu His Leu Asp Gly Asn Lys Ile
                230

Thr Lys Val Asp Ala Ala Ser Leu Lys
235                 240

Gly Leu Asn Asn Leu Ala Lys Leu Gly
    245                 250

Leu Ser Phe Asn Ser Ile Ser Ala Val
        255                 260

Asp Asn Gly Ser Leu Ala Asn Thr Pro
            265                 270

His Leu Arg Glu Leu His Leu Asn Asn
                275

Asn Lys Leu Val Lys Val Pro Gly Gly
280                 285

Leu Ala Asp His Lys Tyr Ile Gln Val
    290                 295

Val Tyr Leu His Asn Asn Asn Ile Ser
        300                 305

Ala Ile Gly Ser Asn Asp Phe Cys Pro
            310                 315
```

```
Pro Gly Tyr Asn Thr Lys Lys Ala Ser
                320

Tyr Ser Gly Val Ser Leu Phe Ser Asn
325                 330

Pro Val Gln Tyr Trp Glu Ile Gln Pro
    335                 340

Ser Thr Phe Arg Cys Val Tyr Val Arg
        345                 350

Ala Ala Val Gln Leu Gly Asn Tyr Lys
            355                 360

<210> 2

<211> 140

<212> PRT

<213> Synthetic peptide - proteolytically
and recombinantly produced

<400> 2

Asp Glu Ala Ser Gly Ile Gly Pro Glu
1               5

Glu Arg Phe His Glu Val Pro Glu Leu
10                  15

Glu Pro Met Gly Pro Val Cys Pro Phe
    20                  25

Arg Cys Gln Cys His Leu Arg Val Val
        30                  35

Gln Cys Ser Asp Leu Gly Leu Glu Lys
            40                  45

Val Pro Lys Asp Leu Pro Pro Asp Thr
                50

Ala Leu Leu Asp Leu Gln Asn Asn Lys
55                  60

Ile Thr Glu Ile Lys Asp Gly Asp Phe
    65                  70

Lys Asn Leu Lys Asn Leu His Thr Leu
        75                  80

Ile Leu Ile Asn Asn Lys Ile Ser Lys
            85                  90

Ile Ser Pro Gly Ala Phe Ala Pro Leu
                95

Val Lys Leu Glu Arg Leu Tyr Leu Ser
100                 105

Lys Asn Gln Leu Lys Glu Leu Pro Glu
    110                 115

Lys Met Pro Lys Thr Leu Gln Glu Leu
        120                 125

Arg Val His Glu Asn Glu Ile Thr Lys
            130                 135

Val Arg Lys Ser Val
                140

<210> 3

<211> 147

<212> PRT

<213> Ovis aries
```

-continued

<400> 3

Asp Glu Ala Ser Gly Ile Gly Pro Glu
1 5

Glu Arg Phe His Glu Val Pro Glu Leu
10 15

Glu Pro Met Gly Pro Val Cys Pro Phe
20 25

Arg Cys Gln Cys His Leu Arg Val Val
30 35

Gln Cys Ser Asp Leu Gly Leu Glu Lys
40 45

Val Pro Lys Asp Leu Pro Pro Asp Thr
50

Ala Leu Leu Asp Leu Gln Asn Asn Lys
55 60

Ile Thr Glu Ile Lys Asp Gly Asp Phe
65 70

Lys Asn Leu Lys Asn Leu His Thr Leu
75 80

Ile Leu Ile Asn Asn Lys Ile Ser Lys
85 90

Ile Ser Pro Gly Ala Phe Ala Pro Leu
95

Val Lys Leu Glu Arg Leu Tyr Leu Ser
100 105

Lys Asn Gln Leu Lys Glu Leu Pro Glu
110 115

Lys Met Pro Lys Thr Leu Gln Glu Leu
120 125

Arg Val His Glu Asn Glu Ile Thr Lys
130 135

Val Arg Lys Ser Val Phe Asn Gly Leu
140

Asn Gln Met
145

<210> 4

<211> 158

<212> PRT

<213> Ovis aries

-continued

<400> 4

Asp Glu Ala Ser Gly Ile Gly Pro Glu
1 5

Glu Arg Phe His Glu Val Pro Glu Leu
10 15

Glu Pro Met Gly Pro Val Cys Pro Phe
20 25

Arg Cys Gln Cys His Leu Arg Val Val
30 35

Gln Cys Ser Asp Leu Gly Leu Glu Lys
40 45

Val Pro Lys Asp Leu Pro Pro Asp Thr
50

Ala Leu Leu Asp Leu Gln Asn Asn Lys
55 60

Ile Thr Glu Ile Lys Asp Gly Asp Phe
65 70

Lys Asn Leu Lys Asn Leu His Thr Leu
75 80

Ile Leu Ile Asn Asn Lys Ile Ser Lys
85 90

Ile Ser Pro Gly Ala Phe Ala Pro Leu
95

Val Lys Leu Glu Arg Leu Tyr Leu Ser
100 105

Lys Asn Gln Leu Lys Glu Leu Pro Glu
110 115

Lys Met Pro Lys Thr Leu Gln Glu Leu
120 125

Arg Val His Glu Asn Glu Ile Thr Lys
130 135

Val Arg Lys Ser Val Phe Asn Gly Leu
140

Asn Gln Met Ile Val Val Glu Leu Gly
145 150

Thr Asn Pro Leu Lys
155

---

SEQUENCE LISTING

<160> NUMBER OF SEQ ID NOS: 4

<210> SEQ ID NO 1
<211> LENGTH: 360
<212> TYPE: PRT
<213> ORGANISM: Ovis aries

<400> SEQUENCE: 1

Met Lys Ala Thr Ile Ile Phe Phe Leu Val Ala Gln Val Ser Trp Ala
1 5 10 15

Gly Pro Phe Gln Gln Lys Gly Leu Phe Asp Phe Met Leu Glu Asp Glu

-continued

```
            20                  25                  30

Ala Ser Gly Ile Gly Pro Glu Glu Arg Phe His Glu Val Pro Glu Leu
        35                  40                  45

Glu Pro Met Gly Pro Val Cys Pro Phe Arg Cys Gln Cys His Leu Arg
    50                  55                  60

Val Val Gln Cys Ser Asp Leu Gly Leu Glu Lys Val Pro Lys Asp Leu
65                  70                  75                  80

Pro Pro Asp Thr Ala Leu Leu Asp Leu Gln Asn Asn Lys Ile Thr Glu
                85                  90                  95

Ile Lys Asp Gly Asp Phe Lys Asn Leu Lys Asn Leu His Thr Leu Ile
            100                 105                 110

Leu Ile Asn Asn Lys Ile Ser Lys Ile Ser Pro Gly Ala Phe Ala Pro
        115                 120                 125

Leu Val Lys Leu Glu Arg Leu Tyr Leu Ser Lys Asn Gln Leu Lys Glu
    130                 135                 140

Leu Pro Glu Lys Met Pro Lys Thr Leu Gln Glu Leu Arg Val His Glu
145                 150                 155                 160

Asn Glu Ile Thr Lys Val Arg Lys Ser Val Phe Asn Gly Leu Asn Gln
                165                 170                 175

Met Ile Val Val Glu Leu Gly Thr Asn Pro Leu Lys Ser Ser Gly Ile
            180                 185                 190

Glu Asn Gly Ala Phe Gln Gly Met Lys Lys Leu Ser Tyr Ile Arg Ile
        195                 200                 205

Ala Asp Thr Asn Ile Thr Thr Ile Pro Gln Gly Leu Pro Pro Ser Leu
    210                 215                 220

Thr Glu Leu His Leu Asp Gly Asn Lys Ile Thr Lys Val Asp Ala Ala
225                 230                 235                 240

Ser Leu Lys Gly Leu Asn Asn Leu Ala Lys Leu Gly Leu Ser Phe Asn
                245                 250                 255

Ser Ile Ser Ala Val Asp Asn Gly Ser Leu Ala Asn Thr Pro His Leu
            260                 265                 270

Arg Glu Leu His Leu Asn Asn Asn Lys Leu Val Lys Val Pro Gly Gly
        275                 280                 285

Leu Ala Asp His Lys Tyr Ile Gln Val Val Tyr Leu His Asn Asn Asn
    290                 295                 300

Ile Ser Ala Ile Gly Ser Asn Asp Phe Cys Pro Pro Gly Tyr Asn Thr
305                 310                 315                 320

Lys Lys Ala Ser Tyr Ser Gly Val Ser Leu Phe Ser Asn Pro Val Gln
                325                 330                 335

Tyr Trp Glu Ile Gln Pro Ser Thr Phe Arg Cys Val Tyr Val Arg Ala
            340                 345                 350

Ala Val Gln Leu Gly Asn Tyr Lys
        355                 360


<210> SEQ ID NO 2
<211> LENGTH: 140
<212> TYPE: PRT
<213> ORGANISM: Ovis aries

<400> SEQUENCE: 2

Asp Glu Ala Ser Gly Ile Gly Pro Glu Glu Arg Phe His Glu Val Pro
1               5                   10                  15

Glu Leu Glu Pro Met Gly Pro Val Cys Pro Phe Arg Cys Gln Cys His
            20                  25                  30
```

```
Leu Arg Val Val Gln Cys Ser Asp Leu Gly Leu Glu Lys Val Pro Lys
        35                  40                  45

Asp Leu Pro Pro Asp Thr Ala Leu Leu Asp Leu Gln Asn Asn Lys Ile
    50                  55                  60

Thr Glu Ile Lys Asp Gly Asp Phe Lys Asn Leu Lys Asn Leu His Thr
65                  70                  75                  80

Leu Ile Leu Ile Asn Asn Lys Ile Ser Lys Ile Ser Pro Gly Ala Phe
                85                  90                  95

Ala Pro Leu Val Lys Leu Glu Arg Leu Tyr Leu Ser Lys Asn Gln Leu
            100                 105                 110

Lys Glu Leu Pro Glu Lys Met Pro Lys Thr Leu Gln Glu Leu Arg Val
        115                 120                 125

His Glu Asn Glu Ile Thr Lys Val Arg Lys Ser Val
    130                 135                 140


<210> SEQ ID NO 3
<211> LENGTH: 147
<212> TYPE: PRT
<213> ORGANISM: Ovis aries

<400> SEQUENCE: 3

Asp Glu Ala Ser Gly Ile Gly Pro Glu Glu Arg Phe His Glu Val Pro
1               5                   10                  15

Glu Leu Glu Pro Met Gly Pro Val Cys Pro Phe Arg Cys Gln Cys His
            20                  25                  30

Leu Arg Val Val Gln Cys Ser Asp Leu Gly Leu Glu Lys Val Pro Lys
        35                  40                  45

Asp Leu Pro Pro Asp Thr Ala Leu Leu Asp Leu Gln Asn Asn Lys Ile
    50                  55                  60

Thr Glu Ile Lys Asp Gly Asp Phe Lys Asn Leu Lys Asn Leu His Thr
65                  70                  75                  80

Leu Ile Leu Ile Asn Asn Lys Ile Ser Lys Ile Ser Pro Gly Ala Phe
                85                  90                  95

Ala Pro Leu Val Lys Leu Glu Arg Leu Tyr Leu Ser Lys Asn Gln Leu
            100                 105                 110

Lys Glu Leu Pro Glu Lys Met Pro Lys Thr Leu Gln Glu Leu Arg Val
        115                 120                 125

His Glu Asn Glu Ile Thr Lys Val Arg Lys Ser Val Phe Asn Gly Leu
    130                 135                 140

Asn Gln Met
145


<210> SEQ ID NO 4
<211> LENGTH: 158
<212> TYPE: PRT
<213> ORGANISM: Ovis aries

<400> SEQUENCE: 4

Asp Glu Ala Ser Gly Ile Gly Pro Glu Glu Arg Phe His Glu Val Pro
1               5                   10                  15

Glu Leu Glu Pro Met Gly Pro Val Cys Pro Phe Arg Cys Gln Cys His
            20                  25                  30

Leu Arg Val Val Gln Cys Ser Asp Leu Gly Leu Glu Lys Val Pro Lys
        35                  40                  45

Asp Leu Pro Pro Asp Thr Ala Leu Leu Asp Leu Gln Asn Asn Lys Ile
    50                  55                  60
```

-continued

```
Thr Glu Ile Lys Asp Gly Asp Phe Lys Asn Leu Lys Asn Leu His Thr
65                  70                  75                  80

Leu Ile Leu Ile Asn Asn Lys Ile Ser Lys Ile Ser Pro Gly Ala Phe
                85                  90                  95

Ala Pro Leu Val Lys Leu Glu Arg Leu Tyr Leu Ser Lys Asn Gln Leu
            100                 105                 110

Lys Glu Leu Pro Glu Lys Met Pro Lys Thr Leu Gln Glu Leu Arg Val
        115                 120                 125

His Glu Asn Glu Ile Thr Lys Val Arg Lys Ser Val Phe Asn Gly Leu
    130                 135                 140

Asn Gln Met Ile Val Val Glu Leu Gly Thr Asn Pro Leu Lys
145                 150                 155
```

The invention claimed is:

1. A method of modulating stem cell recruitment in a subject in need thereof, the method comprising administering to the subject an effective amount of a polypeptide, wherein the polypeptide comprises or consists of:
   (a) the amino acid sequence set forth in amino acid residues 1 to 188 of SEQ ID NO: 1 or an amino acid sequence at least about 95% identical thereto;
   (b) the amino acid sequence set forth in amino acid residues 31 to 188 of SEQ ID NO: 1 or an amino acid sequence at least about 95% identical thereto;
   (c) the amino acid sequence set forth in amino acid residues 1 to 177 of SEQ ID NO: 1 or an amino acid sequence at least about 95% identical thereto;
   (d) the amino acid sequence set forth in amino acid residues 31 to 177 of SEQ ID NO: 1 or an amino acid sequence at least about 95% identical thereto;
   (e) the amino acid sequence set forth in amino acid residues 1 to 170 of SEQ ID NO: 1 or an amino acid sequence at least about 95% identical thereto; or
   (f) the amino acid sequence set forth in amino acid residues 31 to 170 of SEQ ID NO: 1 or an amino acid sequence at least about 95% identical thereto.

2. The method of claim 1, wherein the polypeptide is a fragment of at least 50 or 100 contiguous amino acids and is capable of eliciting cellular chemotaxis and/or inducing localized recruitment of endogenous stem cells.

3. The method of claim 1, wherein the polypeptide consists of the amino acid sequence set forth in SEQ ID NOs: 1, 2, 3, or 4.

4. The method of claim 1, wherein the stem cell recruitment involves angiogenesis, hematopoeisis, protein expression, induction, or deposition, tissue remodelling, repair, or regeneration, cellular proliferation, cellular differentiation, cellular regulation, apoptosis, modulation of one or more immune responses, modulation of tumourigenesis, chemotaxis, or cell recruitment.

5. A method of modulating tissue repair in a subject in need thereof, the method comprising administering to the subject an effective amount of a polypeptide, wherein the polypeptide comprises or consists of:
   (a) the amino acid sequence set forth in amino acid residues 1 to 188 of SEQ ID NO: 1 or an amino acid sequence at least about 95% identical thereto;
   (b) the amino acid sequence set forth in amino acid residues 31 to 188 of SEQ ID NO: 1 or an amino acid sequence at least about 95% identical thereto;
   (c) the amino acid sequence set forth in amino acid residues 1 to 177 of SEQ ID NO: 1 or an amino acid sequence at least about 95% identical thereto;
   (d) the amino acid sequence set forth in amino acid residues 31 to 177 of SEQ ID NO: 1 or an amino acid sequence at least about 95% identical thereto;
   (e) the amino acid sequence set forth in amino acid residues 1 to 170 of SEQ ID NO: 1 or an amino acid sequence at least about 95% identical thereto; or
   (f) the amino acid sequence set forth in amino acid residues 31 to 170 of SEQ ID NO: 1 or an amino acid sequence at least about 95% identical thereto.

6. The method of claim 5, wherein the polypeptide is a fragment of at least 50 or 100 contiguous amino acids and is capable of eliciting cellular chemotaxis and/or inducing localized recruitment of endogenous stem cells.

7. The method of claim 5, wherein the polypeptide consists of the amino acid sequence set forth in SEQ ID NOs: 1, 2, 3, or 4.

8. The method of claim 5, wherein the subject is diagnosed with a disease or disorder associated with a stem cell deficiency.

9. The method of claim 8, wherein the disease or disorder is a disease or disorder associated with a localised stem cell deficiency.

10. A method of modulating stem cell recruitment in a subject in need thereof, the method comprising administering to the subject an effective amount of a mammalian Decorin polypeptide fragment comprising a means for eliciting cellular chemotaxis or cellular recruitment.

11. The method of claim 10, wherein the polypeptide fragment comprises or consists of:
   (a) the amino acid sequence set forth in amino acid residues 1 to 188 of SEQ ID NO: 1 or an amino acid sequence at least about 95% identical thereto;
   (b) the amino acid sequence set forth in amino acid residues 31 to 188 of SEQ ID NO: 1 or an amino acid sequence at least about 95% identical thereto;
   (c) the amino acid sequence set forth in amino acid residues 1 to 177 of SEQ ID NO: 1 or an amino acid sequence at least about 95% identical thereto;
   (d) the amino acid sequence set forth in amino acid residues 31 to 177 of SEQ ID NO: 1 or an amino acid sequence at least about 95% identical thereto;
   (e) the amino acid sequence set forth in amino acid residues 1 to 170 of SEQ ID NO: 1 or an amino acid sequence at least about 95% identical thereto; or (f) the amino acid sequence set forth in amino acid residues 31 to 170 of SEQ ID NO: 1 or an amino acid sequence at least about 95% identical thereto.

* * * * *